(12) United States Patent
Wolff

(10) Patent No.: US 9,400,199 B2
(45) Date of Patent: Jul. 26, 2016

(54) METHOD AND DEVICE FOR THE MEASUREMENT AND THE ELIMINATION OF SYSTEM CHANGES IN A DEVICE FOR THE TREATMENT OF BLOOD

(75) Inventor: Henrik Wolff, Witzenhausen (DE)

(73) Assignee: B. Braun Avitum AG, Melsungen (DE)

( * ) Notice: Subject to any disclaimer, the term of this patent is extended or adjusted under 35 U.S.C. 154(b) by 680 days.

(21) Appl. No.: 13/878,493

(22) PCT Filed: Oct. 14, 2011

(86) PCT No.: PCT/DE2011/001847
§ 371 (c)(1),
(2), (4) Date: Apr. 23, 2013

(87) PCT Pub. No.: WO2012/051996
PCT Pub. Date: Apr. 26, 2012

(65) Prior Publication Data
US 2013/0211730 A1    Aug. 15, 2013

(30) Foreign Application Priority Data

Oct. 14, 2010 (DE) .......................... 10 2010 048 771

(51) Int. Cl.
*G01N 33/48* (2006.01)
*G01F 1/74* (2006.01)
*A61M 1/36* (2006.01)
*G06F 19/00* (2011.01)

(52) U.S. Cl.
CPC ............... *G01F 1/74* (2013.01); *A61M 1/3639* (2013.01); *G06F 19/30* (2013.01); *A61M 2205/702* (2013.01); *A61M 2205/707* (2013.01)

(58) Field of Classification Search
CPC ...................................................... G06F 19/30

USPC ........................................................... 702/19
See application file for complete search history.

(56) References Cited

U.S. PATENT DOCUMENTS

| 5,431,811 | A | 7/1995 | Tusini |
| 5,476,592 | A | 12/1995 | Simard |
| 2003/0136181 | A1 | 7/2003 | Balschat et al. |
| 2005/0102165 | A1* | 5/2005 | Oshita ................ A61M 1/14 705/3 |
| 2006/0157408 | A1 | 7/2006 | Kuroda et al. |
| 2007/0108128 | A1 | 5/2007 | Kopperschmidt et al. |
| 2008/0215247 | A1 | 9/2008 | Tonelli et al. |
| 2010/0137777 | A1 | 6/2010 | Kopperschmidt |

FOREIGN PATENT DOCUMENTS

| DE | 102 01 109 | 1/2003 |
| DE | 103 55 042 | 6/2005 |
| DE | 10355042 | 6/2005 |
| EP | 1 175 917 | 1/2002 |
| EP | 1 364 666 | 11/2003 |
| WO | WO 2006/011009 | 2/2006 |
| WO | WO 2008/135193 | 11/2008 |

OTHER PUBLICATIONS

Chinese Examination Report with translation for CN201180058354.6 dated Dec. 17, 2014.
International Search Report for PCT/DE2013/001847 mailed Jun. 18, 2012.

* cited by examiner

*Primary Examiner* — Jerry Lin
(74) *Attorney, Agent, or Firm* — RatnerPrestia

(57) ABSTRACT

The present invention relates to a method and a device for the measurement of pressure signals in a blood treatment system, whereby system changes can be identified and can be differentiated additionally reliably between system changes in blood flow direction and in transmembrane direction in order to enable a targeted action.

18 Claims, 10 Drawing Sheets

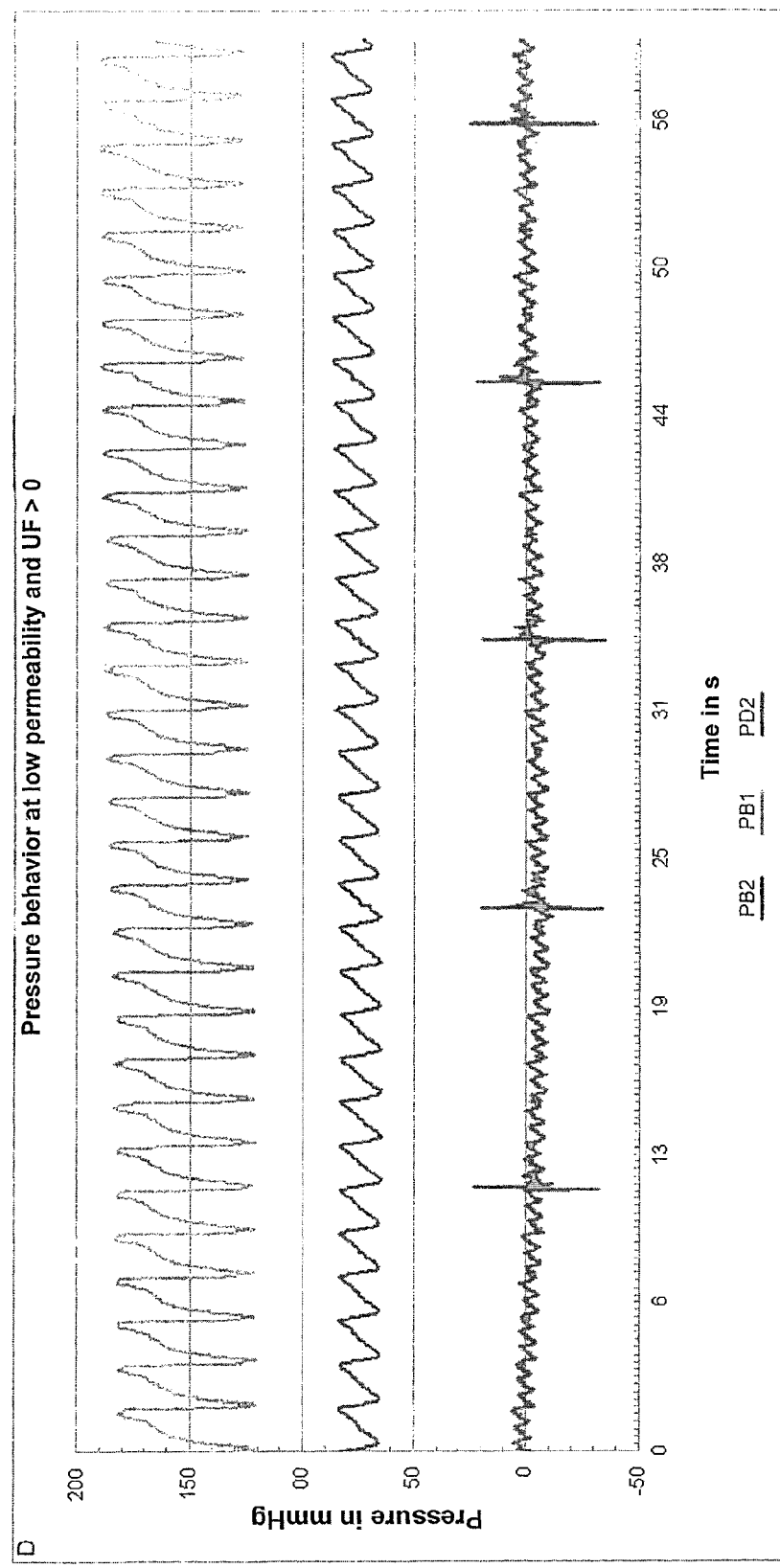

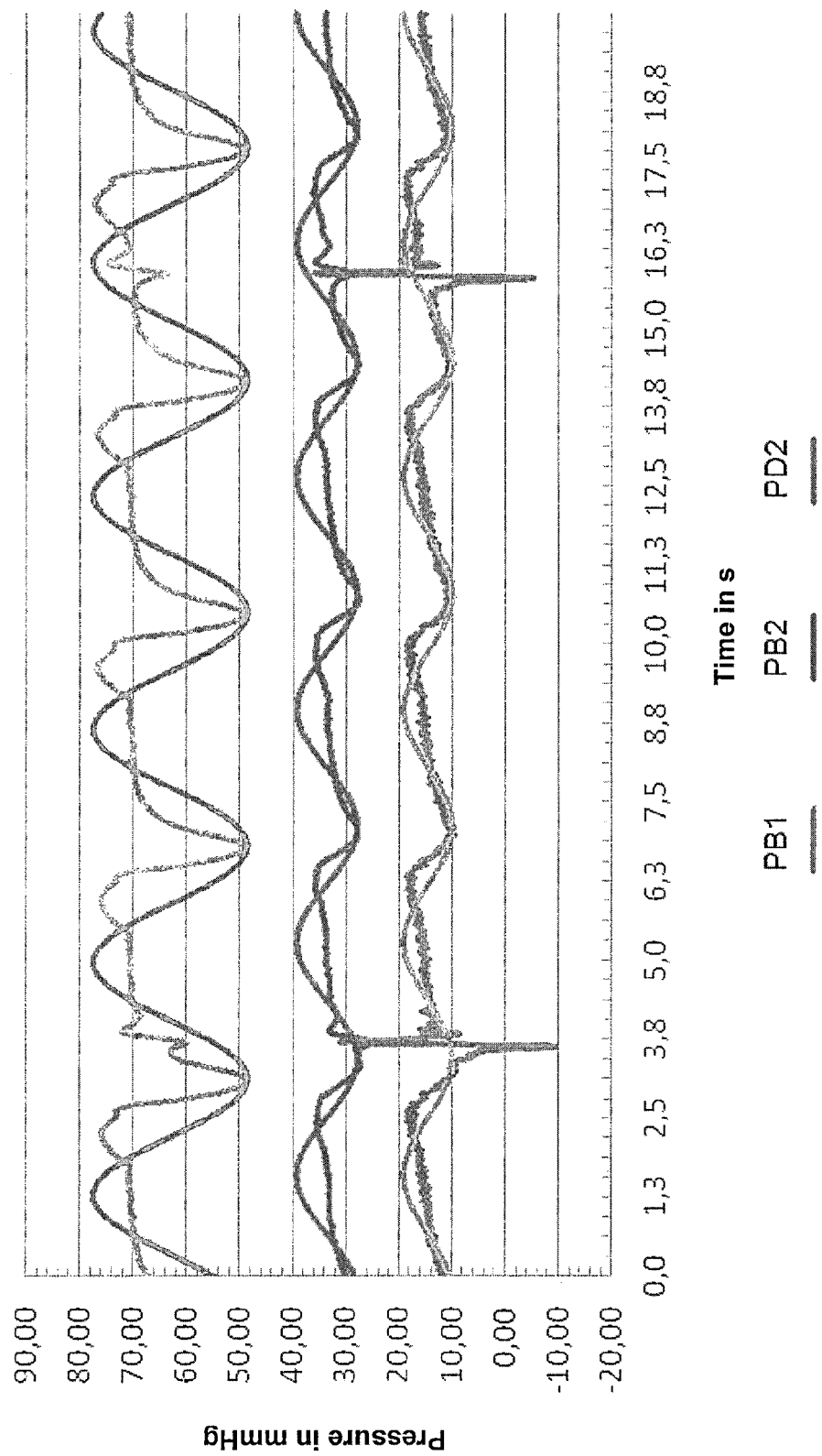

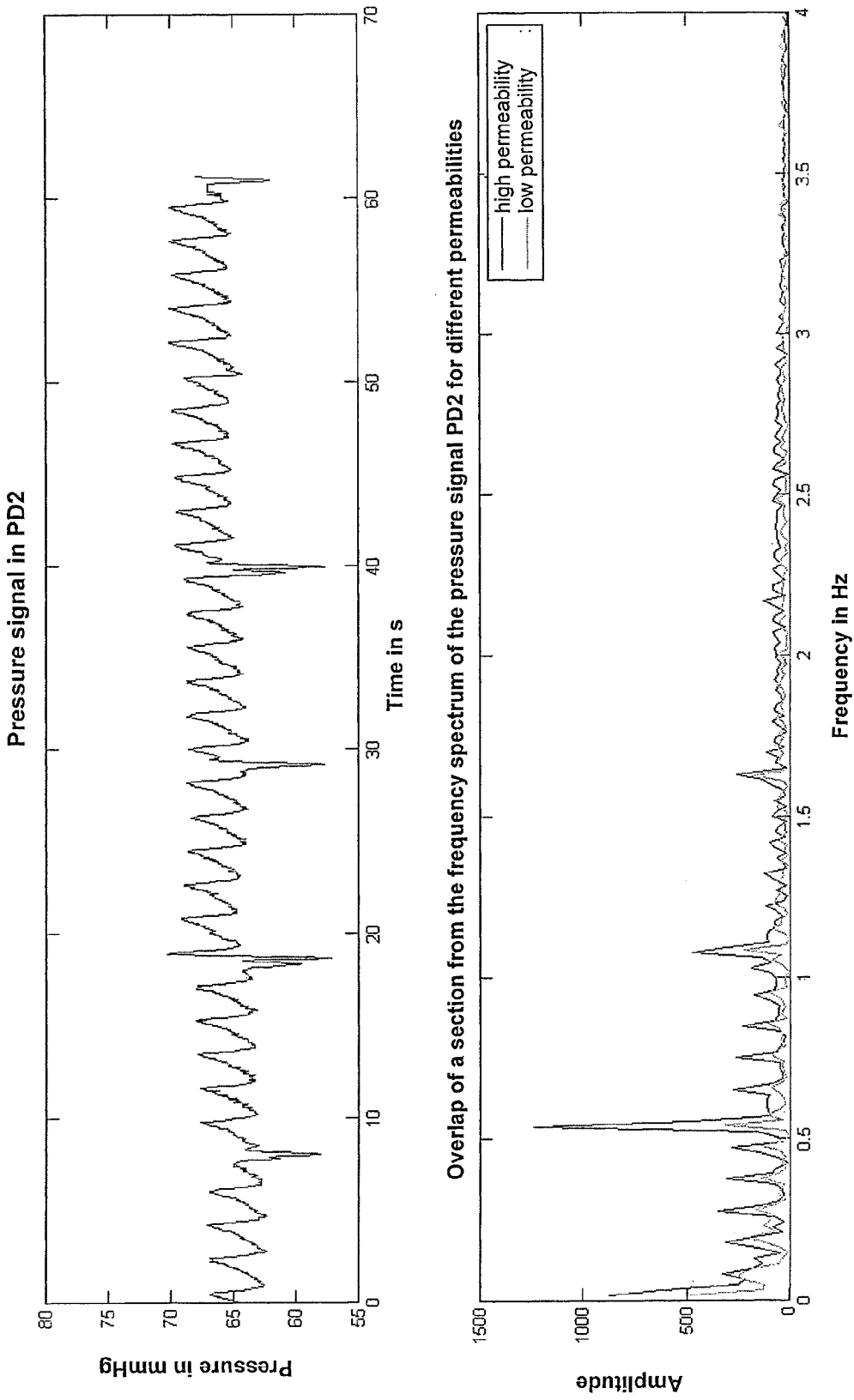

Figure 6

| Pattern constellation of the trends | Trends of the measured pressure signals | | | | Trends of the quotients of the measured pressure signals | | | | | | | | | | | Disturbance / Finding |
|---|---|---|---|---|---|---|---|---|---|---|---|---|---|---|---|---|
| | PB1 | PB2 | PD1 | PD2 | PB1/PB2 | PB1/PD1 | PB1/PD2 | PB1/PDM | PB2/PD1 | PB2/PD2 | PB2/PDM | PBM/PD1 | PBM/PD2 | PBM/PDM | PD1/PD2 | |
| | - | 0 | 0 | 0 | - | - | - | - | 0 | 0 | 0 | - | - | - | 0 | Clotting is reduced |
| | - | - | 0 | 0 | 0 | - | - | - | - | - | - | - | - | - | 0 | Reduction of hemoconcentration |
| | - | - | - | - | ++ | ++ | ++ | ++ | ++ | ++ | ++ | ++ | ++ | ++ | ++ | Acute flow constriction before [PD1] |
| | - | - | 0 | 0 | ++ | - | ++ | - | - | ++ | - | - | ++ | - | ++ | Acute flow constriction between [PD1] and filter |
| | + | 0 | 0 | 0 | + | + | + | + | 0 | 0 | 0 | + | + | + | 0 | Reduced flow area for the blood caused by clotting |
| | + | + | 0 | 0 | 0 | + | + | + | + | + | + | + | + | + | 0 | Higher hemoconcentration |
| | + | 0 | - | - | + | - | - | - | - | - | - | - | - | - | + | Secondary membrane formation |
| | | | | | | | | | | | | | | | | Pressure level on patient side increases (e.g. higher incoming hematocrit value, change of the arm position, flow change in the access) |
| | ++ | 0 | 0 | 0 | ++ | ++ | ++ | ++ | 0 | 0 | 0 | ++ | ++ | ++ | 0 | Tube system between [PB1] and filter clogged |
| | ++ | 0 | ++ | ++ | ++ | 0 | 0 | 0 | - | - | - | - | - | - | 0 | Tube system between filter and [PB2] clogged |
| | ++ | ++ | ++ | ++ | - | - | - | - | - | - | - | - | - | - | - | Tube system after [PB2] clogged or flow change in the access |
| | 0 | 0 | 0 | - | 0 | ++ | ++ | ++ | ++ | ++ | ++ | 0 | ++ | ++ | ++ | Acute flow constriction between filter and [PD2] |

Figure 7

| Trends of the measured pressure signals | | | | Trends of the differences of the measured pressure signals | | | | | | | | | | | Disturbance / Finding |
|---|---|---|---|---|---|---|---|---|---|---|---|---|---|---|---|
| PB1 | PB2 | PD1 | PD2 | PB1-PB2 | PB1-PD1 | PB1-PD2 | PB1-PDM | PB2-PD1 | PB2-PD2 | PB2-PDM | PBM-PD1 | PBM-PD2 | PBM-PDM | PD1-PD2 | |
| - | 0 | 0 | 0 | - | - | - | - | 0 | 0 | 0 | - | - | - | 0 | Clotting is reduced |
| - | - | 0 | 0 | 0 | - | - | - | - | - | - | - | - | - | 0 | Reduction of hemoconcentration |
| -- | -- | -- | -- | 0 | 0 | 0 | 0 | 0 | 0 | 0 | 0 | 0 | 0 | 0 | Acute flow constriction before [PD1] |
| - | - | 0 | -- | 0 | - | 0 | - | - | 0 | - | - | 0 | - | ++ | Acute flow constriction between [PD1] and filter |
| + | 0 | 0 | 0 | + | + | + | + | 0 | 0 | 0 | + | + | + | 0 | Reduced flow area for the blood caused by clotting |
| + | + | 0 | 0 | 0 | + | + | + | + | + | + | + | + | + | 0 | Higher hemoconcentration |
| + | 0 | - | - | + | + | + | + | + | + | + | + | + | + | 0 | Secondary membrane formation |
| + | + | + | + | 0 | 0 | 0 | 0 | 0 | 0 | 0 | 0 | 0 | 0 | 0 | Pressure level on patient side increases (e.g. higher incoming hematocrit value, change of the arm position, flow change in the access) |
| ++ | 0 | 0 | 0 | ++ | ++ | ++ | ++ | 0 | 0 | 0 | ++ | ++ | ++ | 0 | Tube system between [PB1] and filter clogged |
| ++ | 0 | ++ | ++ | ++ | 0 | 0 | 0 | - | - | - | - | - | - | 0 | Tube system between filter and [PB2] clogged |
| ++ | ++ | ++ | ++ | 0 | 0 | 0 | 0 | 0 | 0 | 0 | 0 | 0 | 0 | 0 | Tube system after [PB2] clogged or flow change in the access |
| 0 | 0 | 0 | - | 0 | 0 | ++ | ++ | 0 | ++ | ++ | 0 | ++ | ++ | ++ | Acute flow constriction between filter and [PD2] |

Pattern constellation of the trends

METHOD AND DEVICE FOR THE MEASUREMENT AND THE ELIMINATION OF SYSTEM CHANGES IN A DEVICE FOR THE TREATMENT OF BLOOD

CROSS REFERENCE TO RELATED APPLICATIONS

This application is the U.S. national phase application of PCT International Application No. PCT/DE2011/001847 filed Oct. 14, 2011, which claims priority to German Patent Application No. 10 2010 048 771.6 filed Oct. 14, 2010, the contents of each application being incorporated by reference herein.

FIELD OF THE INVENTION

The present invention relates to a method for the detection of system changes in a device for the treatment of blood and a device for the treatment of blood.

The invention relates also to the field of the filtration, more precisely said the tangential flow filtration (TFF). Here, the fluid to be purified is separated by a semipermeable membrane from the purification solution. Typically, the purification solution has a lower concentration of substances than that of substances to be removed from the fluid to be purified. Hereby diffusion is generated. To use optimally the diffusion as purification force, tangential flow filters are typically operated by the countercurrent principle.

A dialysis filter consists substantially of hollow fibers, i.e. cylindrical fibers, which cross stretched longitudinally a housing. Thereby, the walls of the hollow fibers work through semipermeable structures as membranes. At their ends, the hollow fibers are embedded in a casting compound. In the dialysis filter, the hollow fibers can be combined into modules with several square meter filter surface. In the dialysis by tangential flow filtration, also known as cross-flow filtration, blood/plasma is supplied to the hollow fibers by a first fluid circulation, which flows through them lengthwise. By a second fluid circulation, the dialysate is supplied usually by the countercurrent principle, but if possible also parallel to the blood stream. The housing thus has four ports, namely for each fluid stream two, one for the supply and removal, respectively. On the inside of the hollow fiber membrane is thus the blood stream, and on the outside is the dialysate.

Another purification mechanism is convection. Here is a pressure gradient across the semipermeable membrane is generated, whereby the fluid to be purified is pressed over the semipermeable membrane. Thereby, the substances are washed away in its current concentration. This purification process is not dependent on the concentration of substances in the purification solution, decisive here are only the concentration in the fluid to be purified, and the membrane properties, such as sieving coefficient, permeability etc. It is therefore of interest to know the filter properties at the beginning as well as during the treatment.

A specific area of the filtration is the extracorporeal blood treatment for chronic or acute renal failure. Here, the fluid to be purified is the blood of the patient and the purification solution is the dialysate. Decisive in this specific case of the TFF it is to replace in the treatments (in the chronic case typically three times pro week) the blood purification function of the kidney as effective as possible. To ensure this, the Kt/V value has been established as measure of the treatment quality. The Kt/V is a parameter to determine the dialysis effectiveness and a key element for the evaluation of the dialysis efficiency. K is the clearance, which is determined by the urea content of the blood before and after the dialysis. The value t shows the effective dialysis time in minutes and the V is the urea distribution volume. This refers to 60% of the body mass (weight), in which the blood can circulate (body water content). The aim of a treatment is to archive to a Kt/V≥1.2. In a normal treatment process values are archived, which meet this criterion in general. However, adversities can occur in a treatment, which affect negatively the treatment process as well as the treatment result. It is therefore important to monitor and control the influencing parameters during a treatment in order to react to such adversities in a fast and especially targeted manner and to adjust the system parameters during the dialysis accordingly.

A decisive process is the interaction of the filter membrane with blood. Through this interaction the flow properties of the filter deteriorate both in transmembrane direction and in blood flow direction. These changes are caused for example by thrombocyte attachment on the membrane, clot formation, chemical binding of blood components to the membrane or simply mechanical (flow conditional) pressing of the blood components on and even into the membrane.

Transmembrane direction or transmembranous here refers to a flow of the blood over the membrane of the dialyzer or dialysis filter.

During clot formation a gelatinous aggregation of red blood cells (erythrocytes) stabilized by fibrin is formed. Unlike the term thrombus a coagulum describes a blood clot, which is located outside of a blood or lymph vessel (extravascular) and not inside (intravascular).

These and other changes of the system properties have various effects on the treatment process and the treatment, quality. Especially, the treatment by hemodiafiltration is affected thereby, because here it is focused on the convective substance transport of medium molecular substances. By deterioration of the transmembrane flow properties or the permeability, also the sieving coefficient for uremic substances in the medium molecular weight range deteriorates, which has the result that by the same amount of convectively filtered fluid less uremic substances are removed from the blood circulation. Another effect is the reduction of the effective flow area, both in blood flow direction and in transmembrane direction. This results in a reduction of the active filter surface whereby it can lead to a deterioration of the diffusive purification. With new filter there is usually a buffering potential that is larger than the maximum physiological filtering. Thereby, a reduction of the effective flow area can be limited in a certain degree. However, if this potential is exhausted, it leads to the above-described effect.

Purging with saline for the "cleaning" of the dialyzer, the addition of heparin to prevent further clot formation or the lowering of the ultrafiltration rate (UF) in order to reduce the hemoconcentration are generally accepted as suitable counteractions, or reactions to such changes. The permeability of the membranes is determined by measuring the fluid volume, which run at a given pressure difference at a temperature of 37° C. through a predetermined membrane surface through the membrane and which is normalized for general comparability in terms of area unit, time unit, and pressure unit. As fluid for determining the ultrafiltration rate water is used.

DESCRIPTION OF THE RELATED ART

From the prior art experiments are already known which have the aim to recognize system changes and react to them. In the US 2008/0215247 A1 it is assumed that the linear relationship between transmembrane pressure (TMP) and ultrafiltration rate $Q_{UF}=TMP*K_{UF}$ ($K_{UF}$=ultrafiltration coefficient) is fulfilled only in a certain range of the TMP. Thus, at first the function $Q_{UF}$ (TMP) is estimated by increasing the TMP gradually and measuring the thereby generated ultrafiltration rate. From a certain value an increase of TMP results in an ever less increase of the ultrafiltration rate. Therefrom the knee point (tangent point) of the function $Q_{UF}$ (TMP) is selected as working point. Since the $K_{UF}$ deteriorates during the treatment due to the system change, the WO 2006/011009 A2 discloses the technical conditions to determine the relationship between TMP and $Q_{UF}$ hourly basis.

In the EP 1175917 A1 as a further concept is described the adjustment of the ratios from pre- and postdilution in the process of the treatment.

In the US 2006/157408 A1 a method for the detection of filter cloggings is disclosed. To detect such filter cloggings, up to four different pressure sensors are used, which take pressure measurements at up to four different positions. For pressure changes at one of the pressure sensors it is concluded that a filter clogging is present on which it can be reacted by addition of heparin. However, it was not recognized that a plurality of combinations exist in which the pressures in the system can change without that it would actually have come to a filter clogging. Furthermore, it was not recognized that these constellations can be recognized only by the generation of time trends from the measured pressure signals and all quotients or differences of the measured pressure signals. In the present invention it has been found that pressure differences are not always due to filter clogging, but can have a plurality of causes, which can be detected according to aspects of the invention and narrowed down locally. Although the US 2006/157408 A1 discloses that at up to four positions pressure measurements can be made in order to increase the safety of the yes-no statement met, but the pressures are not set in relation to each other and trends are not observed in order to detect thereby different disturbance patterns and to limit locally. Thus, the four measuring points only serve to make the statement on whether the filter is clogged or not (yes-no statement), which would have been found even only with the measurement at a measuring point. I.e. the measurement which is carried out in the US 2006/157408 A1 at up to four measuring points, is not used to obtain more information, but only to increase the measurement accuracy, because for example, during the measurement at only one point the measuring sensor may be damaged, which could be recognized by the measurement at several points. According to aspects of the invention the measurement at the four measuring points does not serve to increase the measurement accuracy, but rather to obtain more information in order to limit the error source locally and additionally describe the disturbance qualitatively.

Further, in the DE 10355042 B3 a method is disclosed with which disturbances in the blood flow can be detected, in which the phase angle of at least one harmonic component of an oscillating pressure signal propagating in the extracorporeal blood circulation is determined. Also with this method disturbances in the system cannot be accurately detected and limited locally and as only measure for the elimination of a disturbance, just the control of the ultrafiltration rate is stated.

SUMMARY OF THE INVENTION

An object of this invention is thus to provide a method for the detection of system changes in a device for the treatment of blood, and a device for the treatment of blood suitable for the measurement of these system changes in the device for the treatment of blood, which can not only identify system changes, but also additionally distinguish reliably between system changes in blood flow direction, dialysate flow direction and transmembrane direction in order to enable a targeted action.

An object is solved according to aspects of the invention by the methods and the devices which are mentioned in the independent claims. Further advantageous embodiments of the invention result from the dependent claims, the description, the figures as well as the examples.

Method for the differentiation of disturbances of the flow resistance in a blood treatment system comprising the following steps:

The inventive method for the detection of system changes and particularly for differentiation of disturbances of the flow resistance in a blood treatment system comprises the following steps:

a) measuring at least two pressure signals selected from the group consisting of (PB1, PB2, PD1, PD2), which are measured at least two pressure sensors, which are selected from the group consisting of [PB1], [PB2], [PD1] and [PD2], wherein [PB1] represents the pressure sensor in the blood circulation before the blood inlet into the tangential flow filter TFF and PB1 represents the pressure measured at the pressure sensor [PB1], [PB2] represents the pressure sensor in the blood circulation after the blood outlet from the tangential flow filter TFF and PB2 represents the pressure measured at the pressure sensor [PB2], [PD1] represents the pressure sensor in the dialysate circulation before the dialysate inlet into the tangential flow filter TFF and PD1 represents the pressure measured at the pressure sensor [PD1] and [PD2] represents the pressure sensor in the dialysate circulation after the dialysate outlet from the tangential flow filter TFF and PD2 represents the pressure measured at the pressure sensor [PD2];

b) calculating the quotients and/or the differences from the pressure signals measured according to step a), wherein the quotients and/or the differences are calculated from the pressure signals selected from the group consisting of (PB1, PB2) and/or (PB1, PD1) and/or (PB1, PD2) and/or (PB2, PD1) and/or (PB2, PD2) and/or (PD1, PD2) and/or (PB1, PDM) and/or (PB2, PDM) and/or (PD1, PBM) and/or (PD2, PBM) and/or (PDM, PBM) in a central processing unit, wherein with PBM or PDM the respective average value from (PB1,PB2) or (PD1, PD2) is represented;

c) at least one time-shifted repeating of the steps a) and b), wherein it is measured at the same at least two pressure sensors as in the previous measurement and from the measured pressure signals the same quotients and/or differences are calculated;

d) generating at least one time trend from the measured pressure signals selected from the group consisting of (PB1, PB2, PD1, PD2) and/or the calculated differences, and/or quotients of the pressure signals (PB1, PB2) and/ or (PB1, PD1) and/or (PB1, PD2) and/or (PB2, PD1) and/or (PB2, PD2) and/or (PD1, PD2) and/or (PB1, PDM) and/or (PB2, PDM) and/or (PD1, PBM) and/or (PD2, PBM) and/or (PDM, PBM);

e) evaluating the at least one time trend, whether a change of the at least one time trend has occurred beyond a tolerance range;

f) generating a pattern for the evaluation of the at least one time trend;

g) assigning the pattern to a disturbance condition; and h) displaying the disturbance on a display device of the central processing unit.

In a preferred manner, by the inventive method a statement can be made whether the flow properties have changed in blood flow direction, in dialysate flow direction as well as in transmembrane direction. Previous systems are not able to make such a differentiation. Further preferred, by the inventive method disturbances cannot only be narrowed down locally, it is also possible in many cases to detect the cause of the disturbance qualitatively. This offers the advantage that by analysis of the at least two pressure signals, the type and location of the change in the device for the treatment of blood can be determined accurately in order to carry out subsequently a targeted elimination of the cause for the change. A costly and time-consuming search for the exact problem underlying the change is omitted. General measures such as the purging of the entire device for the treatment of blood can be replaced by targeted measures, by, for example, changing only the tube system or only the filter, in which a system change, for example, in the form of a clot formation has occurred.

Optionally, this method can comprise additionally the following step:

i) elimination of the disturbance of the flow resistance in transmembrane direction, dialysate flow direction or blood flow direction or indication of a possibility for the elimination of the disturbance.

The elimination of the disturbance can be performed automatically, semi-automatically or manually, unless it is the replacement of system components such as dialyzer or tube system. Furthermore, the displaying of the evaluation according to step h) and the indication of a possibility for the elimination of the disturbance according to step i) can be performed at the same time or immediately successively or two steps can also be identical. If the disturbance should be eliminated only by complete replacement of a system component, the replacement of the dialyzer is manual, or if an automatic elimination of disturbance should be desired, the blood flow and optionally also the dialysate flow is diverted to a replacement component located on or in the dialysis device.

In a further preferred embodiment the time trend is generated from the measured pressure signals and the calculated differences, and/or quotients of the pressure signals, or only with the calculated differences, and/or quotients. In this embodiment, step d) is replaced by the following step d'):

d') generating at least one time trend from the measured pressure signals selected from the group consisting of: (PB1, PB2, PD1, PD2) and the calculated differences, and/or quotients of the pressure signals (PB1, PB2) and/or (PB1, PD1) and/or (PB1, PD2) and/or (PB2, PD1) and/or (PB2, PD2) and/or (PD1, PD2) and/or (PB1, PDM) and/or (PB2, PDM) and/or (PD1, PBM) and/or (PD2, PBM) and/or (PDM, PBM), or the calculated differences and/or quotients of the pressure signals (PB1, PB2) and/or (PB1, PD1) and/or (PB1, PD2) and/or (PB2, PD1) and/or (PB2, PD2) and/or (PD1, PD2) and/or (PB1, PDM) and/or (PB2, PDM) and/or (PD1, PBM) and/or (PD2, PBM) and/or (PDM, PBM).

The step d') recites the same as step d) only in a more detailed notation.

In a further embodiment the inventive method comprises the measurement of at least three pressure signals and also the following steps:

a) measuring at least three pressure signals selected from the group consisting of (PB1, PB2, PD1, PD2), which are measured at least three pressure sensors, which are selected from the group consisting of [PB1], [PB2], [PD1] and [PD2], wherein [PB1] represents the pressure sensor in the blood circulation before the blood inlet into the tangential flow filter TFF and PB1 represents the pressure measured at the pressure sensor [PB1], [PB2] represents the pressure sensor in the blood circulation after the blood outlet from the tangential flow filter TFF and PB2 represents the pressure measured at the pressure sensor [PB2], [PD1] represents the pressure sensor in the dialysate circulation before the dialysate inlet into the tangential flow filter TFF and PD1 represents the pressure measured at the pressure sensor [PD1] and [PD2] represents the pressure sensor in the dialysate circulation after the dialysate outlet from the tangential flow filter TFF and PD2 represents the pressure measured at the pressure sensor [PD2];

b) calculating the quotients and/or the differences from the pressure signals measured according to step a), wherein the quotients and/or the differences are calculated from the pressure signals selected from the group consisting of (PB1, PB2) and/or (PB1, PD1) and/or (PB1, PD2) and/or (PB2, PD1) and/or (PB2, PD2) and/or (PD1, PD2) and/or (PB1, PDM) and/or (PB2, PDM) and/or (PD1, PBM) and/or (PD2, PBM) and/or (PDM, PBM) in a central processing unit, wherein with PBM or PDM the respective average value from (PB1,PB2) or (PD1, PD2) is represented;

c) at least one time-shifted repeating of the steps a) and b), wherein it is measured at the same at least three pressure sensors as in the previous measurement and from the measured pressure signals the same quotients and/or differences are calculated;

d) generating at least one time trend from the measured pressure signals selected from the group consisting of: (PB1, PB2, PD1, PD2) and/or the calculated differences, and/or quotients of the pressure signals (PB1, PB2) and/or (PB1, PD1) and/or (PB1, PD2) and/or (PB2, PD1) and/or (PB2, PD2) and/or (PD1, PD2) and/or (PB1, PDM) and/or (PB2, PDM) and/or (PD1, PBM) and/or (PD2, PBM) and/or (PDM, PBM);

e) evaluating the at least one time trend, whether a change of the at least one time trend has occurred beyond a tolerance range;

f) generating a pattern for the evaluation of the at least one time trend;

g) assigning the pattern to a disturbance condition; and h) displaying the disturbance on a display device of the central processing unit.

In a most preferred embodiment the inventive method comprises the measurement of four pressure signals and can be represented as follows.

Method for the differentiation of disturbances and/or changes of the flow resistance in a blood treatment system comprising the following steps:

a) measuring four pressure signals (PB1, PB2, PD1, PD2), which are measured at four pressure sensors ([PB1], [PB2], [PD1] and [PD2]), wherein [PB1] represents the pressure sensor in the blood circulation before the blood inlet into the tangential flow filter TFF and PB1 represents the pressure measured at the pressure sensor [PB1], [PB2] represents the pressure sensor in the blood circulation after the blood outlet from the tangential flow filter TFF and PB2 represents the pressure measured at the pressure sensor [PB2], [PD1] represents the pressure sensor in the dialysate circulation before the dialysate inlet into the tangential flow filter TFF and PD1 represents the pressure measured at the pressure sensor [PD1] and [PD2] represents the pressure sensor in the dialysate circulation after the dialysate outlet from the tangential flow filter TFF and PD2 represents the pressure measured at the pressure sensor [PD2];

b) calculating the quotients and/or the differences from the pressure signals measured according to step a), wherein the quotients and/or the differences are calculated from the pressure signals selected from the group consisting of (PB1, PB2) and (PB1, PD1) and (PB1, PD2) and (PB2, PD1) and (PB2, PD2) and (PD1, PD2) and (PB1, PDM) and (PB2, PDM) and (PD1, PBM) and (PD2, PBM) and (PDM, PBM) in a central processing unit, wherein with PBM or PDM the respective average value from (PB1,PB2) or (PD1, PD2) is represented;

c) at least one time-shifted repeating of the steps a) and b), wherein it is measured at the same four pressure sensors as in the previous measurement and from the measured pressure signals the same quotients and/or differences are calculated;

d) generating the time trends from the measured pressure signals (PB1, PB2, PD1, PD2) and/or the calculated differences, and/or quotients of the pressure signals (PB1, PB2) and (PB1, PD1) and (PB1, PD2) and (PB2, PD1) and (PB2, PD2) and (PD1, PD2) and (PB1, PDM) and (PB2, PDM) and (PD1, PBM) and (PD2, PBM) and (PDM, PBM);

e) evaluating the time trends, whether a change of the time trends has occurred beyond a tolerance range;

f) generating a pattern for the evaluation of the time trends;

g) assigning the pattern to a disturbance condition; and h) displaying the disturbance on a display device of the central processing unit.

In this embodiment in the blood treatment system four pressure signals PB1, PB2, PD1 and PD2 are measured. The measurement is performed at the pressure sensors [PB1], [PB2], [PD1] and [PD2], wherein [PB1] represents the pressure sensor in the blood circulation before the blood inlet into the tangential flow filter TFF and PB1 represents the pressure measured at the pressure sensor [PB1], [PB2] represents the pressure sensor in the blood circulation after the blood outlet from the tangential flow filter TFF and PB2 represents the pressure measured at the pressure sensor [PB2], [PD1] represents the pressure sensor in the dialysate circulation before the dialysate inlet into the tangential flow filter TFF and PD1 represents the pressure measured at the pressure sensor [PD1] and [PD2] represents the pressure sensor in the dialysate circulation after the dialysate outlet from the tangential flow filter TFF and PD2 represents the pressure measured at the pressure sensor [PD2].

From the measured pressure signals in the next step in a central processing unit every possible combination from quotients and/or differences is calculated, which are formed from the four pressure signals. This means concretely that quotients and/or differences are calculated from the pressure signals (PB1, PB2), (PB1, PD1), (PB1, PD2), (PB2, PD1), (PB2, PD2), (PD1, PD2), (PB1, PDM), (PB2, PDM), (PD1, PBM), (PD2, PBM) and (PDM, PBM). Thus, there are now all quotients and/or differences from the pressure signals for the first measurement.

In the next step a re-measurement at the four pressure sensors is carried out, which takes place time-shifted to the first measurement. This measurement is performed identically to the first measurement, i.e. at the same pressure sensors, with the same configurations, only with the difference, that the pressure signals are measured time-shifted to the first measurement. From the pressure signals measured now time-shifted analogously to the above-described calculation in a central processing unit, every possible combination of quotients and/or differences is calculated, which can be formed from the four pressure signals measured time-shifted. This means concretely that quotients and/or differences are calculated from the pressure signals measured time-shifted (PB1, PB2), (PB1, PD1) (PB1, PD2), (PB2, PD1), (PB2, PD2), (PD1, PD2), (PB1, PDM), (PB2, PDM), (PD1, PBM), (PD2, PBM) and (PDM, PBM). Thus, there are now the quotients and/or differences from the pressure signals measured time-shifted for the second measurement.

Generally, it should be noted that the inventive methods require in the above-mentioned combination of pressure signals that in repeated or analogous measurements and calculations, the same measurement and calculation is carried out. In particular, the formation of the quotient should not comprise once a/b and in the re-measurement b/a, but continuously a/b. The same applies mutatis mutandis for the formation of the differences: if in the first measurement a−b is formed, also a−b is formed for the re-measurement and not b−a.

In further time-shifted measurements further pressure signals can be measured and further quotients and/or differences from the pressure signals can be calculated, however according to aspects of the invention the above-mentioned two measurements are sufficient to perform the method. For the determination of a trend, theoretically any number of measurements at different times can be included, wherein the time period which is selected for the calculation of a trend should be clearly less than one-tenth ($\frac{1}{10}$) of the duration of the dialysis session, preferably less than one-fiftieth ($\frac{1}{50}$), more preferably less than $\frac{1}{80}$, more preferably less than $\frac{1}{100}$, more preferably less than $\frac{1}{110}$, more preferably less than $\frac{1}{120}$ of duration of the dialysis session. Within the considered time period for the calculation of a trend can be 2 to 60,000 time-shifted measurements of pressure signals, preferably 3 to 20,000, more preferably 4 to 10,000, still more preferably 5 to 5,000 measurements.

From the measured pressure signals of the first and second pressure measurement and all quotients and/or differences of the first measurement and the second measurement a time trend is now calculated, i.e. that the quotient, and/or the difference of the pressure signals (PB1, PB2) from the first measurement is compared with the quotient and/or the difference of the pressure signals (PB1, PB2) from the second measurement. This time trend is generated for each of the quotients and/or differences of the pressure signals from the first measurement and the quotient and/or differences of the pressure signals from the second measurement. Furthermore, the time trend of the pressure signals is generated for each of the pressure signals PB1, PB2, PD1 and PD2. Thus, now there are time trends for the measured pressure signals and each quotients and/or differences of the pressure signals from the first and the second measurement. Each time trend is evaluated in terms of whether a change has occurred beyond a tolerance range. Also, each trend can be classified in terms of whether there has been no change which goes beyond a tolerance range, whether the trend is increasing, that is, goes beyond the tolerance range at the upper limit, or whether the trend is decreasing, that is, goes beyond the tolerance range at the lower limit. From the evaluation of each time trend results a pattern that can be assigned to a specific distribution condition.

For example, the measurement of the pressure signals at time point t=0 s and further time-shifted measurement at the time points t=60 s, t=120 s, t=180 s, t=240 s and t=300 s could have resulted in the following values:

| | PB1 [mmHG] | PB2 [mmHG] | PD1 [mmHG] | PD2 [mmHG] |
|---|---|---|---|---|
| t = 0 s | 120 | 50 | 80 | 70 |
| t = 60 s | 125 | 49 | 79 | 70 |
| t = 120 s | 133 | 51 | 78 | 70 |
| t = 180 s | 139 | 48 | 80 | 69 |
| t = 240 s | 145 | 52 | 81 | 70 |
| t = 300 s | 150 | 50 | 80 | 71 |

From the measured values now for each of the time-shifted measurements all possible quotients and/or differences are formed. For the time point t=0, this would mean that quotients and/or differences are calculated from (PB1, PB2), (PB1, PD1), (PB1, PD2), (PB2, PD1), (PB2, PD2), (PD1, PD2), (PB1, PDM), (PB2, PDM), (PD1, PBM), (PD2, PBM) and (PDM, PBM). This would lead for the time point t=0 to the following result for the quotient formation: ($120/50$), ($120/80$), ($120/70$), ($50/80$), ($50/70$), ($80/70$), ($120/75$), ($50/75$), ($80/85$), ($70/85$) and ($75/85$). The calculation is performed also for the difference, and is carried out for each of the time-shifted measurements. From the calculated quotients and/or differences, and/or the absolute measured values, trends for the absolute values and/or the quotients and/or differences are now generated. For the quotient of (PB1, PB2) herewith the following time trend could result: ($120/50$), ($125/49$), ($133/51$), ($139/48$), ($145/52$) and ($150/50$). This time trend is generated for each quotient and/or the differences, and/or the absolute values. This results in the present example that the time trend t=0 to t=300 s is increasing for the quotients from (PB1, PB2), (PB1, PD1), (PB1, PD2), (PB1, PDM), (PBM, PD1), (PBM, PD2) and (PBM/PDM), wherein the remaining time trends of the quotients are unchanged. Furthermore, it is possible to generate trends within trends. This would mean in the present example that not only a time trend between t=0 and t=300 s is generated, but that also any number of time trends between t=0 and t=240 s, or t=60 s and t=180 s, etc. can be generated. The generation of long-term trends is naturally better suitable for the detection of disturbances that occur more gradually, wherein with shorter trends also disturbances can be detected, which are of minor nature. The pattern constellation shown in this example from the trends of the quotients and/or the differences, and/or the absolute values is specific for a secondary membrane formation. For all possible disturbance conditions, there are now specific pattern constellations that are formed from the formation of the trends from the quotients and/or the trends of the differences and/or the trends of the absolute values. For example, such pattern constellations are listed in the FIGS. 6 and 7.

In another embodiment, the measurement of the at least two pressure signals is performed simultaneously. In this embodiment step a) is replaced by the following step a'):

a') measuring at least two pressure signals selected from the group consisting of (PB1, PB2, PD1, PD2), which are measured simultaneously at least two pressure sensors, which are selected from the group consisting of [PB1], [PB2], [PD1] and [PD2], wherein [PB1] represents the pressure sensor in the blood circulation before the blood inlet into the tangential flow filter TFF and PB1 represents the pressure measured at the pressure sensor [PB1], [PB2] represents the pressure sensor in the blood circulation after the blood outlet from the tangential flow filter TFF and PB2 represents the pressure measured at the pressure sensor [PB2], [PD1] represents the pressure sensor in the dialysate circulation before the dialysate inlet into the tangential flow filter TFF and PD1 represents the pressure measured at the pressure sensor [PD1] and [PD2] represents the pressure sensor in the dialysate circulation after the dialysate outlet from the tangential flow filter TFF and PD2 represents the pressure measured at the pressure sensor [PD2];

With "simultaneously" as used herein, it is meant that the pressure signals are measured at the same time or immediately successively. This is that there is no longer delay between the measurement of the one pressure signal and of the other pressure signal or of the other pressure signals. Preferably, the measurement of the pressure signals is performed within a period of 5 minutes, preferably 1 minute, more preferably within 45 seconds, even more preferably within 30 s, more preferably within 15 s, and most preferably within the periods less than or equal to 1 s.

In principle, the inventive method can be performed with at least two pressure sensors, wherein preferably three pressure sensors and more preferably four pressure sensors are used.

The tangential flow filter is one of the most common filter types that can be used in a device for the treatment of blood. In principle, other filter types can be also used without that the inventive method would be impaired in some way. Therefore, the invention does not only relate to dialysis devices with a tangential flow filter, but with any type of dialyzer.

According to aspects of the invention the pressure signals are measured and all possible quotients and/or differences from the measured pressure signals are calculated, i.e. in the use of two pressure sensors two pressure signals are measured, from which the quotient and/or the difference are formed. This means that in the use of the pressure sensors [PB1] and [PD1] the pressure signals PB1 and PD2 are measured, and the quotients and/or the differences are calculated from (PB1, PD1). If three pressure sensors are used, then at each of these pressure sensors a pressure signal is measured, for which then with each of the other pressure signals a quotient or the difference are calculated. For example, the pressure signals PB1, PB2 and PD1 could be measured, from which then the quotients and/or differences are calculated from (PB1, PB2), (PB1, PD1), (PB2, PD1) and (PBM, PD1). For the case that four pressure sensors are used, the quotient and/or the difference for each possible pair of the four pressure signals is calculated. Additionally, average values for the two pressure signals on dialysate side and the two pressure signals on blood side are calculated, for which then with each of the pressure signals quotients and/or differences can be calculated, i.e. concretely that the quotients and/or differences are calculated from (PB1, PB2), (PB1, PD1), (PB1, PD2), (PB2, PD1), (PB2, PD2), (PD1, PD2), (PB1, PDM), (PB2, PDM), (PD1, PBM), (PD2, PBM), and (PDM, PBM). With PBM or PDM, the respective average value from pressure signals on blood and dialysate side is represented.

The at least one time-shifted measurement is performed in each case with the same number and the same pressure sensors, as used in the previous measurement. The time-shifted measurement is performed under the same conditions, i.e. with the same configurations, with the only difference that they are performed time-shifted. Thus, by the time-shifted measurement for each of the pressure sensors a further time-shifted pressure signal is obtained. According to aspects of the invention at least one time-shifted measurement must be performed. In practice, it has been found that several time-shifted measurements are advantageous in order to detect disturbances of the flow resistance in a blood treatment system. This is performed advantageously over the whole period of the treatment with the blood treatment system in order to ensure that also over the whole period disturbances in the system can be detected. Thus time-shifted means that between each measurement there is a certain time period that can be determined individually. Hereby, this can mean very rapid measurements, such as 20 times per second, but it is also possible that the measurements are carried out over a longer time period, such as a measurement every 5 minutes, a measurement every minute, a measurement every 30 seconds, a measurement every 10 seconds, a measurement every second or a measurement every tenth of a second.

Preferably, the measured pressure signals are normalized in order to eliminate the normal pressure fluctuations, which are caused for example, by the pump.

The generation of the time trend includes the comparison of the measured pressure signals and/or the quotients and/or the differences from the measurements in terms of whether changes have occurred in the measured pressure signals and/ or the quotients, and/or the differences over time. For the generation of the time trend, according to aspects of the invention, at least two time-shifted measurements must be performed at the pressure sensors. The time trends are generated thereby for each of the measured pressure signals and/or the quotients and/or the differences, i.e. with four pressure sensors and thereby four measured pressure signals all possible quotients and/or differences are formed from the four measured pressure signals. According to aspects of the invention, at least once the four pressure signals are measured time-shifted at the four pressure sensors, from which quotients and/or differences are formed anew. Each of the measured pressure signals and/or the quotients and/or the differences from the first measurement is then compared with the measured pressure signals and/or the quotients and/or the differences from the time-shifted measurement, thus for each of the measured pressure signals and/or the quotients and/or the differences, a time trend is obtained.

If several time-shifted measurements have been performed, according to aspects of the invention there are for each of these time points several measured pressure signals and/or quotients and/or differences. It is at the skilled person's discretion, whether preferably "short" time trends should be detected, which consist of only a few time-shifted measurements, or whether long-term time trends should be detected, which consist of a plurality of time-shifted measurements. The generation of the time trend can in principle be performed also by comparison of the measured pressure signals and/or of the quotients and/or differences over all time-shifted measurements. But it is also possible that the time trend is generated only for a few of these time-shifted measurements. Specifically, this means that small deviations in principle can be better detected by the generation of "short" trends, which consist of only a few time-shifted measurements, wherein gradual, continuous changes in the system can be better detected by the generation of long-term trends, which includes a plurality of time-shifted measured pressure signals and/or quotients and/or differences. According to aspects of the invention, both short and long-term time trends can be generated and combined with each other.

In Practice it was found that the generation of the time trends should be started only after a preliminary lead time of ca. 1-5 minutes, since depending on the hematocrit, the ultrafiltration rate, the specific filter that is used, that is, especially the number of fibers in the filter, the flow rate and generally the viscosity of the blood, it takes a while until stable pressure signals can be measured, from which then the time trends for the measured pressure signals and/or quotients and/or differences can be generated.

The evaluation of the time trends is performed in such manner that is registered whether a change of the time trend beyond a tolerance range has occurred. Hereby it is distinguished between time trends which increase fast (++), increase (+), remain unchanged (0), decrease (−) and those that decrease fast (−−).

The tolerance range can for example be limited in such way that in the small time trend, consisting of the measured pressure signals and/or the quotients and/or the differences of two time-shifted measurements, a change of the measured pressure signals and/or the quotients and/or differences by 10%, in one or the other direction, either as an increase (+) or a decrease (−) of the time trends are evaluated. In contrast, any fluctuations within this tolerance range are evaluated as "remained unchanged (0)". Thus, the tolerance range is the range in which the values of the measured pressure signals and/or the quotients and/or the differences can be located in order to be evaluated as "remained unchanged (0)". Values that are outside the tolerance range are changed so that the time trend is then evaluated accordingly. In order that a time trend is evaluated as rapidly increasing (++) or rapidly decreasing (−−), an acute change must occur between the time-shifted determined measured pressure signals and/or the quotients and/or differences, i.e. the change should not evolve over a longer period of time, but must occur abruptly. This is particularly the case, when e.g. a tube is snapped off. The threshold for distinguishing between increasing or decreasing as well as fast increasing or fast decreasing signals, can be determined according to the machine type, patient, preferred analysis parameters etc. individually.

The limit of the tolerance range is dependent on a certain number of factors, such as the hematocrit, the ultrafiltration rate, the specific filter that is used, i.e. in particular the number of fibers in the filter, the flow rate and generally the viscosity of the blood. The tolerance range can e.g. be limited in such way that the measured pressure signals and/or quotients and/ or differences should not exceed or fall below an absolute value within the time trend. On the other hand, the tolerance range can be also selected so that, for example a certain percentage in change of the measured pressure signals and/or quotients and/or differences should not exceed. Naturally, several limits for tolerance ranges can be combined, for example in that it is determined that the tolerance range is limited by an upper absolute value as well as by changes in percent of the measured pressure signals and/or the quotients and/or the differences. In such a case, a time trend could be thus, e.g. evaluated as increasing (+), in which it exceeds either the upper absolute limit or the limit of changes in percent of the measured pressure signals and/or the quotients and/or the differences. It is within the skill of the person skilled in the art to determine tolerance ranges without being inventive.

From the evaluation of the time trends, a pattern is resulted, which can be assigned to a specific disturbance condition. Thus, it may happen for example that the quotient from PB1/ PD1 has a decreasing trend, wherein the quotient form PB2/ PD2 has a constant trend. The entity of the evaluated time trends results also in a pattern. In the FIG. 6-7 exemplary some pattern constellations are compiled for occurring pressure changes in the operation of a dialysis device and the disturbances underlying them.

Especially it is preferred when at least one pressure signal on the blood side and at least one other pressure signal on the dialysate side are determined. More preferred it is when one pressure signal on the blood side and two pressure signals on the dialysate side or two pressure signals on the blood side and one pressure signal on the dialysate side are determined. In a particularly preferred embodiment, two pressure signals on the blood side, and two pressure signals on the dialysate side are determined. The pressure measurements are performed preferably at or directly in front of the inlets and outlets of the tangential flow filter (TFF).

In the measured pressure signals, it can be absolute pressures, relative pressures, absolute pressure differences between two pressure measuring points, relative pressure differences between two pressure measuring points, absolute pressure amplitudes, relative pressure amplitudes, differences between the absolute pressure amplitudes at two pressure measuring points, or differences between the relative pressure amplitudes at two pressure measurement points or a combination thereof, or the frequency spectra of the pressures.

The term "absolute pressure" or "absolute pressures", as used herein, describes the pressure compared to the atmospheric pressure.

The term "relative pressure" or "relative pressures", as used herein, describes the relative change of a pressure signal in relation to a second pressure signal.

The term "pressure difference" or "pressure differences", as used herein, describes the difference of two pressures.

The term "pressure amplitude" or "pressure amplitudes", as used herein, describes the determined or measured value of the pressure fluctuations. As synonym the "term pressure swing amplitude" can be used.

The term "frequency spectrum" or "frequency spectra", as used herein, describes the entity of the frequency which are generated by a swinging system or are included in a signal.

It has been surprisingly found that the measurement and analysis of the pressure signals, for example generated also by a blood pump P in the system, provides information about the flow properties in a device for the treatment of blood by formation of the quotients and/or differences from the measured pressure signals, from which a time trend is derived, which has a specific pattern for specific disturbance conditions. According to aspects of the invention, each pressure signal in the system can be used for the analysis regardless of its origin. For example, in one embodiment, the pressure signals, which are generated by the switching of a balance chamber BK, are determined and used for the analysis.

The monitoring of the system properties during the treatment is preferably implemented such that the pressure signals generated by the blood pump P and their propagation are monitored. According to aspects of the invention, also the pressure signals of a pump on dialysate side or the pressure peaks produced by the switching of valves are monitored. It is also possible to monitor combined pressure signal from both pumps, or detect each single pressure signal. Especially preferred is the monitoring of the four pressure signals at the inputs and outputs of the tangential flow filter TFF.

Depending on the system properties of the blood treatment system, the pressure signals spread in the system along the blood flow direction and transmembrane direction.

It is thus possible to register changes of the flow conditions by monitoring the pressure signals on the blood side and the dialysate side as well as by monitoring the ratios of these pressures and to differentiate between changes in the blood flow direction, dialysate flow direction and transmembrane direction.

The term "blood treatment unit" describes thereby a device that can be used for the purification and/or treatment of blood, whose centerpiece is a tangential flow filter. In particular, it can be a dialysis unit, which is capable of hemodialysis, hemoperfusion, hemofiltration, or hemodiafiltration.

The term "system change", as used herein, comprises inter alia the interaction of components of the apparatus for the treatment of blood, particularly, of the filter membrane with blood. By this interaction the flow properties deteriorate both in transmembrane direction and in blood flow direction. This is caused for example by thrombocyte attachment, clot formation, chemical binding of blood components to the membrane or simply mechanical (flow conditional) pressures of the blood components to and even into the membrane, but is not limited to this and can also occur at other positions within the blood treatment unit. Furthermore, changes in the system are comprised, as they can occur for example, by the snapping off a tube or a leak in the system. Those are considered system changes, although no direct interaction of the components of the apparatus with blood occurs.

The determination of the pressure signals is performed via pressure sensors. For this, the pressure sensors known from the prior art can be used, such as piezoresistive, piezoelectric, frequency-analogous, pressure sensors with Hall elements, capacitive, inductive and/or combinations thereof. Preferred are pressure sensors, whose sampling rate is at least 20 Hz. The sampling rate describes herein the rate with which the signal values are taken from a continuous signal.

The relationships according to aspects of the invention are represented in detail as shown in FIGS. 6 and 7:

If for example, the filter membrane is clogged by clotting, an increasing trend of the measured pressure signal PB1 is shown at the pressure sensor [PB1], wherein the trends of the other pressure signals PB2, PD1 and PD2 remain unchanged. By the subsequent calculation of the quotients and/or the differences of the measured pressure signals and the generation of the time trends a much more differentiated picture appears which shows that the time trends of the quotients and/or differences from (PB1, PB2), (PB1, PD1), (PB1, PD2), (PBM, PD1), (PDM, PD2), (PWM/PDM) increase, whereas the time trends of the quotients and/or differences of (PB2, PD1), (PB2, PD2), (PB2, PDM) and (PD1, PD2) remains unchanged. From the entity of the trends of the measured pressure signals and/or the trends of the quotients and/or the trends of the differences of the measured pressure signals results a characteristic pattern constellation which can be assigned directly to the disturbance condition clotting.

The single value (pressure signal) itself is subject to many influences and by the observation of the current value little information is obtained. Therefore, according to aspects of the invention it has been recognized that only by the formation of the quotients and/or differences of the pressure signals and the generation of a time trends, disturbances can be detected in detail. Changes in this time trend are different in various disturbance conditions and result in a specific pattern, which can be assigned to the respective disturbance condition. For example system changes due to the treatment can be distinguished from those (changes) due to external influences.

The differentiation between the formation of quotients and differences of the pressure signals therefore makes sense, since for a pressure change by an offset, such as an increased resistance in the backflow, the pressure signals change at the same absolute value which leads to that the differences remain constant, but the quotients change, whereby also these disturbances can be detected according to aspects of the invention.

Other disturbances could e.g. occur in the form of an acute flow constriction before [PD1] or acute flow constriction between [PD1] and filters. According to aspects of the invention, here it can be distinguished between the two disturbances. With an acute flow constriction before [PD1] all pressure sensors show rapidly a decreasing trend of the measured pressure signals. Only by the further calculation of the quotient and the differences of the measured pressure signals and the generation of the time trends, a more differentiated pattern results which shows that the time trends of the quotient of the measured pressure signals have all an increasing trend, whereas the time trends of the differences show no change. From the entity of the trends of the measured pressure signals and the trends of the quotients and the trends of the differences of the measured pressure signals, now results the characteristic pattern constellation which can be assigned directly to the disturbance pattern acute flow constriction before [PD1].

The disturbance acute flow constriction between [PD1] and filter, however, is characterized in that in an acute flow constriction between [PD1] and filter at all pressure sensors, a fast decreasing trend of the measured pressure signals is shown, except at the pressure sensor [PD1] which remains unchanged. The further calculation of the quotients and the differences of the measured pressure signals and the generation of the time trends shows in this case that the time trends of the quotients of the measured pressure signals (PB1, PB2), (PB1, PD2), (PB2, PD2), (PBM, PD2) and (PD1, PD2) increase, whereas the time trends of the quotient of the measured pressure signals (PB1, PD1), (PB1, PDM), (PB2, PD1), (PB2, PDM), (PBM, PD1) and (PBM, PDM) decrease. In this relationship, the time trends of the differences show another pattern. Here, the difference of the time trends (PD1, PD2) increases fast, the differences of the time trends of (PB1, PB2), (PB1, PD2), (PB2, PD2) and (PBM, PD2) remain unchanged, whereas the differences of the time trends (PB1, PD1), (PB1, PDM), (PB2, PD1), (PB2, PDM), (PBM, PD1) and (PBM, PDM) decrease fast. From the entity of the trends of the measured pressure signals and the trends of the quotients and the trends of the differences of the measured pressure signals, now result the characteristic pattern constellation which can be assigned directly to the disturbance condition acute flow constriction between [PD1] and filter.

According to aspects of the invention not only disturbances are detected in the sense and evaluated qualitative, but it is also possible to detect and evaluate qualitatively the findings which are not a disturbance. These findings are according to aspects of the invention also system changes, which represent indeed no disturbances, wherein however, it can still make sense to detect these findings and to notify the operator of the blood treatment system.

Such a finding may be for example, if by a measure clotting could be reduced. The reduction of the clotting represents according to aspects of the invention that at the pressure sensor [PB1] a decreasing trend of the measured pressure signals is determined, whereas the measured pressure signals of the other pressure sensors have an unchanged time trend. From the further calculation of the quotients and/or the differences of the measured pressure signals and the generation of the time trends results a much more differentiated pattern, which shows that the time trends of the quotients and/or differences from (PB1, PB2), (PB1, PD1), (PB1, PD2), (PBM, PD1), (PDM, PD2) and (PBM/PDM) decrease, whereas the time trends of the quotients and/or differences from (PB2, PD1), (PB2, PD2), (PB2, PDM) and (PD1, PD2) remain unchanged. From the entity of the trends of the measured pressure signals and the trends of the quotients and/or the trends of the differences of the measured pressure signals results a characteristic pattern constellation which can be assigned directly to the finding "clotting reduced".

Such findings represent thereby valuable information for the operator of the blood treatment system, since they can provide inter alia information about whether an initiated measure has also been successful.

The transmembrane flow resistance is determined from the difference of the measured pressure signals from PB1 and PD2 and/or the ratio from PB1 and PD2 and/or the difference from PB2 and PD2 and/or the ratio from PD2 and PB2. Furthermore, changes of the pressure amplitudes $A_{PD2}$ and/or the ratio of the pressure amplitudes $A_{PB1}$ and $A_{PD2}$ and/or the ratio of the pressure amplitudes $A_{PB2}$ and $A_{PD2}$ and/or the difference from PB1 and PD1 and/or the ratio from the PB1 and PD1 and/or the difference from PB2 and PD1 and/or the ratio from the PB2 and PD1 and/or the change of the pressure amplitude $A_{PB1}$ and $A_{PD1}$ and/or the ratio of the pressure amplitudes $A_{PB1}$ and $A_{PD1}$ and/or the ratio of the pressure amplitudes $A_{PB2}$ and $A_{PD1}$ serve as indicator for the transmembrane flow resistance.

As [PB1] is described the pressure sensor in the blood circulation before the blood inlet into the tangential flow filter TFF and with PB1 the pressure measured at pressure sensor [PB1]. As [PB2] is described the pressure sensor in the blood circulation after the blood outlet from the tangential flow filter TFF and with PB2 the pressure measured at pressure sensor [PB2]. As [PD1] is described the pressure sensor in the dialysate circulation before the dialysate inlet into the tangential flow filter TFF and as PD1 the pressure measured at pressure sensor [PD1]. As [PD2] is described the pressure sensor in the dialysate circulation after the dialysate outlet from the tangential flow filter TFF and PD2 the pressure measured at pressure sensor [PD2].

As PBM or PDM is described the respective average value of PB1 and PB2 or PD1 and PD2.

Previous approaches could not differentiate between changes in blood flow direction, dialysate flow direction, and transmembrane direction, whereby a targeted elimination of disturbances was not possible. By the use of up to four pressure sensors and the analysis of the detected pressure signals at each of these pressure sensors, all abovementioned ratios can be monitored. From the entity of the pressure signals a full analysis can be performed, which enable to determine targeted the type of system change. By an appropriate analysis of four pressure signals, the situation of the disturbance can be limited at least.

Preferably, the pressure signals are determined on blood side at the pressure sensor [PB1] as well as at the pressure sensor [PB2]. On dialysate side, the pressure signals are determined preferably at the pressure sensor [PD2] and at the pressure sensor [PD1].

In an alternative embodiment, however it is sufficient, if there are the pressure signals PB1 and PB2 and one of the signals PD1 or PD2 on dialysate side.

The analysis of the determined pressure signals is performed via devices which are known to the skilled person in the art from the prior art. The device for the analysis of the measured data can be for example, a CUP which calculates changes of the measured pressure signals to predetermined reference value and/or changes to previously measured initial values. The analysis can be performed in the form of absolute and/or relative changes, differences in the measured values, changes in the pressure amplitudes, for example, the height of the amplitudes and/or the frequency spectrum.

In a preferred embodiment, the analysis of the pressure signals is performed at a central processing unit. This central processing unit comprises a CPU, an input for the measured pressure values, and a display for the measured pressure values and/or the determined recommendations for actions.

The effectivity of the blood treatment depends primarily on four factors: the treatment time, the blood flow, the clearance and the dialysate flow. Especially the sufficiently long treatment time must be guaranteed and is a major factor for a successful treatment. Numerous studies have shown that the higher administered dialysis dose, the lower is the patient mortality (over a broad correlation range).

Failures due to disturbances in the operation accumulate quickly to several sessions per year. In extreme cases, sessions must be even interrupted. Much more often, however, are the cases in which a disturbance is not detected and therefore not eliminated, which leads to a suboptimal dialysis result. By a targeted elimination of disturbances these timeouts are reduced to a minimum and can be avoided in some cases even completely by initiating the proper measure during the running operation. The search for the cause of the disturbance is omitted as far as possible and gives thus also the patients an increased feeling of security. Consequently, the dialysis efficiency increases and the economic efficiency of dialysis is also improved.

The term "flow properties", as used herein, refers to the entity of the properties of the respective flowing fluid. Of particular interest are the dynamic viscosity, the flow rate, the flow volume, the flow profile, osmotic pressure, the surface tension as well as the changes generated by the used pumps as well as the active operating elements such as electric devices and passive operating elements such as the tube system and the dialyzer, and artifacts.

The term "ratio", as used herein, is not obligatorily limited to the quotients from two factors, but can also comprise the difference or any other index, with which the "ratio" between two factors is expressed.

The analysis of frequency spectrum of individual pressure signals has also shown that a change of the permeability affects the amplitudes of the harmonic frequencies. The same applies to flow changes in blood flow direction.

In a preferred embodiment, the frequency spectrum of individual signals as well as the relative change with respect to a second signal is determined. By analysis of the two frequency spectra, a statement about the flow properties in blood flow direction, dialysate flow direction or in transmembrane direction can be made, wherein blood flow direction and transmembrane direction are preferred.

In another embodiment, the pressure signals of a blood pump are determined for the inventive differentiation of system changes.

In another embodiment, the pressure signals of a balance chamber are determined for the inventive differentiation of system changes.

In another embodiment, the method for the measurement of pressure signals in a blood treatment system increases the dialysis efficiency and economic efficiency of the dialysis by differentiation between system changes that occur in blood flow direction or in transmembrane direction.

In all methods described herein, it is preferred, to measure more than two pressure signals, and in particular four pressure signals at the same time or time-shifted at the inlets and outlets of the tangential flow filter TFF, as taken by the pressure sensors [PB1], [PB2], [PD1] and [PD2].

The invention comprises further also a device for the measurement of pressure signals in a device for the treatment of blood, which increases the dialysis efficiency and economic efficiency of dialysis, by differentiation between system changes that occur in blood flow direction or in transmembrane direction, comprising at least two pressure sensors for the measurement of pressure signals.

All above-described embodiments and advantages refer advantageously also to the method and the device for the measurement of pressure signals in a blood treatment system, which increases the dialysis efficiency and economic efficiency of dialysis, by differentiation between system changes that occur in the blood flow direction or in transmembrane direction.

The composition of the pressure signals is not significant for the inventive method. According to aspects of the invention, pressure signals can be used from single sources, but also pressure signals that represents the sum of a plurality of sources.

In some embodiments it can be advantageous, when from the sum of the pressure signals only one is determined or from the sum of the pressure signals only one is filtered in order to determine a valid value for the remaining pressure signals. This can be for example the case, when a very irregular pressure signal would overlap the measurement of the others or when a certain pressure signal is especially suitable for the measurement due to its properties. Such devices for the correction of the pressure signals are well known from the prior art.

Further, an object of the present invention is solved by the method according to claim 1.

In a preferred embodiment, on blood side a pressure sensor [PB1] between a pump P and a filter TFF and a further pressure sensor [PB2] between the filter TFF and the patient ☺ are installed and on dialysate side a pressure sensor [PD2] behind the outlet of the filter TFF and one further pressure sensor [PD1] before the inlet into the filter TFF are installed.

In another embodiment the apparatus according to aspects of the invention comprises a device for the analysis of the measured data. This can be a CPU that calculates changes of the measured pressure signals to predetermined reference values and/or changes to previously measured initial values.

In a preferred embodiment the device for the treatment of blood comprises a tangential flow filter TFF, a pump P, and at least two pressure sensors ([PB1], [PB2] or [PD1], [PD2] or [PB1], [PD1] or [PB1], [PD2] or [PB2], [PD1] or [PB2], [PD2]), wherein the pressure sensors ([PB1], [PB2] or [PD1], [PD2] or [PB1], [PD1] or [PB1], [PD2] or [PB2], [PD1] or [PB2], [PD2]) are located directly upstream and/or directly downstream to the tangential flow TFF.

In a further preferred embodiment the device for the treatment of blood comprises a tangential flow filter TFF, a pump P, and at least three pressure sensors ([PB1], [PB2], [PD1] or [PB1], [PB2], [PD2] or [PD1], [PD2], [PB1] or [PD1], [PD2], [PB2]), wherein the pressure sensors ([PB1], [PB2], [PD1] or [PB1], [PB2], [PD2] or [PD1], [PD2], [PB1] or [PD1], [PD2], [PB2]) are located directly upstream and/or directly downstream to the tangential flow TFF.

Even more preferred is a device for the treatment of blood comprising a tangential flow filter TFF, a pump P, and four pressure sensors [PB1], [PB2], [PD1] and [PD2], wherein the pressure sensors [PB1], [PD1] are located directly upstream to the tangential flow filter TFF and the pressure sensors [PB2], [PD2] are located directly downstream to the tangential flow filter TFF.

If at least one pressure signal is used, which should be determined at several time points successively in order to be related to each other in the form of a quotient or a difference, and in a second calculating step this sensor-specific quotients or differences are related to other sensor-specific quotients or differences, the steps of method are as follows (method 2):

a) time-shifted measuring of each of at least two pressure signals at least two pressure sensors,
wherein the pressure signals are selected from the group consisting of PB1, PB2, PD1 and PD2, the pressure sensors are selected from the group consisting of [PB1], [PB2], [PD1] and [PD2],

[PB1] represents the pressure sensor in the blood circulation before the blood inlet into the tangential flow filter TFF and PB1 represents the pressure measured at the pressure sensor [PB1],

[PB2] represents the pressure sensor in the blood circulation after the blood outlet from the tangential flow filter TFF and PB2 represents the pressure measured at the pressure sensor [PB2],

[PD1] represents the pressure sensor in the dialysate circulation before the dialysate inlet into the tangential flow filter TFF and PD1 represents the pressure measured at the pressure sensor [PD1], and

[PD2] represents the pressure sensor in the dialysate circulation after the dialysate outlet from the tangential flow filter TFF and PD2 represents the pressure measured at the pressure sensor [PD2];

b) calculating of at least two quotients and/or differences from the pressure signals measured time-shifted according to step a) at the same pressure sensor in a central processing unit, wherein the quotients calculated in such a manner according to the pressure sensor, at which the measurement has been carried out, are represented as Q[PB1], Q[PB2], Q[PD1] and Q[PD2] and the differences as Δ[PB1], Δ[PB2], Δ[PD1] and Δ[PD2];

c) calculating at least one quotient and/or at least one difference in the central processing unit from the quotients and/or differences calculated according to step b), wherein the quotients and/or the differences are selected from the group consisting of (Q[PB1], Q[PB2]) and/or (Q[PB1], Q[PD1]) and/or (Q[PB1], Q[PD2]) and/or (Q[PB2], Q[PD1]) and/or (Q[PB2], Q[PD2]) and/or (Q[PD1], Q[PD2]) and/or (Δ[PB1], Δ[PB2]) and/or (Δ[PB1], Δ[PD1]) and/or (Δ[PB1], Δ[PD2]) and/or (Δ[PB2], Δ[PD1]) and/or (Δ[PB2], Δ[PD2]) and/or (Δ[PD1], Δ[PD2]) and/or (Q[PB1], (Δ[PB1]) and/or (Q[PB1], (Δ[PB2]) and/or (Q[PB1], (Δ[PD1]) and/or (Q[PB1], (Δ[PD2]) and/or (Q[PB2], (Δ[PB1]) and/or (Q[PB2], (Δ[PB2]) and/or (Q[PB2], (Δ[PD1]) and/or (Q[PB2], (Δ[PD2]) and/or (Q[PD1], (Δ[PB1]) and/or (Q[PD1], (Δ[PB2]) and/or (Q[PD1], (Δ[PD1]) and/or (Q[PD1], (Δ[PD2]) and/or (Q[PD2], (Δ[PB1]) and/or (Q[PD2], (Δ[PB2]) and/or (Q[PD2], (Δ[PD1]) and/or (Q[PD2], (Δ[PD2]) and/or (Q[PB1], Q[PBM]) and/or (Q[PB2], Q[PBM]) and/or (Q[PD1], Q[PBM]) and/or (Q[PD2], Q[PBM]) and/or (Δ[PB1], Q[PBM]) and/or (Δ[PB2], Q[PBM]) and/or (Δ[PD1], Q[PBM]) and/or (Δ[PD2], Q[PBM]) and/or (Q[PB1], Q[PDM]) and/or (Q[PB2], Q[PDM]) and/or (Q[PD1], Q[PDM]) and/or (Q[PD2], Q[PDM]) and/or (Δ[PB1], Q[PDM]) and/or (Δ[PB2], Q[PDM]) and/or (Δ[PD1], Q[PDM]) and/or (Δ[PD2], Q[PDM]) and/or (Q[PB1], Δ[PBM]) and/or (Q[PB2], Δ[PBM]) and/or (Q[PD1], Δ[PBM]) and/or (Q[PD2], Δ[PBM]) and/or (Δ[PB1], Δ[PBM]) and/or (Δ[PB2], Δ[PBM]) and/or (Δ[PD1], Δ[PBM]) and/or (Δ[PD2], Δ[PBM]) and/or (Q[PB1], Δ[PDM]) and/or (Q[PB2], Δ[PDM]) and/or (Q[PD1], Δ[PDM]) and/or (Q[PD2], Δ[PDM]) and/or (Δ[PB1], Δ[PDM]) and/or (Δ[PB2], Δ[PDM]) and/or (Δ[PD1], Δ[PDM]) and/or (Δ[PD2], Δ[PDM]) and/or (Q[PBM], Q[PDM]) and/or (Q[PBM], Δ[PBM]) and/or (Q[PBM], Δ[PDM]) and/or (Q[PDM], Δ[PBM]) and/or (Q[PDM], Δ[PDM]) and/or (Δ[PBM], Δ[PDM]) and wherein Q[PBM] represents the average value from Q[PB1] and Q[PB2], Q[PDM] represents the average value from Q[PD1] and Q[PD2], Δ[PBM] represents the average value from Δ[PB1] and Δ[PB2], Δ[PDM] represents the average value from Δ[PD1] and Δ[PD2];

d) at least one time-shifted repeating of the steps a), b) and c), wherein it is measured at the same at least two pressure sensors as in the previous measurement and from the measured pressure signals the same quotients and/or differences are calculated;

e) generating at least one time trend from the measured pressure signals selected from the groups listed in c);

f) evaluating the at least one time trends, whether a change of the at least one time trend has occurred over a tolerance range;

g) generating a pattern for the evaluation of the at least one time trend;

h) assigning the pattern to a disturbance condition and i) displaying the disturbance on a display device of the central processing unit.

This embodiment is only a complement of the above-described main method of this invention. Here, before the calculating step of above-described main method, only the calculating step of the time-shifted measurement at least two pressure sensors is preceded. With this alternative method, some disturbances in the dialysis process, which can be already detected and located by the first method, can be displayed more accurately in cases of doubt.

For the sake of clarity, the quotients calculated in this additional computational step are described in accordance with the pressure sensor, at which they are determined, as Q[PB1], Q[PB2], Q[PD1] and Q[PD2] and the differences are described as Δ[PB1], Δ[PB2], Δ[PD1] and Δ[PD2].

It goes without saying that only these combinations can be calculated, which are logically possible from the preselection of the number of repeated measurements and the number of pressure sensors in order to carry out the method according to aspects of the invention.

Optionally, this method can comprise additionally the following step:

j) elimination of the disturbance of the flow resistance in transmembrane direction, dialysate flow direction or blood flow direction or indication of a possibility for the elimination of the disturbance.

With respect to the steps i) and j) the same applies in analogy as set forth above for the method 1.

On the central processing unit tolerance ranges for the evaluation of the time trend of the measured pressure signals and/or the quotients and/or differences from the pressure signals can be already stored. This time trends of the measured pressure signals and/or quotients and/or the differences of the pressure signals can be derived from one or more prior sessions of a certain patient with this specific dialyzer. Optionally also measured values of this patient of other dialysis devices can be used, likewise measured values of this specific dialysis device which are not patient-specific. Reference values known from the literature or machine-specific specifications of the manufacturer of the dialysis device may also be used.

With "directly" it is meant that there is no other component between the pressure sensor and the said component. The actual distance between the pressure sensor and said component is herein not decisive, rather only that the pressure sensor and said component are not separated by a further intermediate component. According to aspects of the invention, two pressure sensors are never located directly after one another i.e. without a further component between the pressure sensors. Moreover the present invention does not use a pressure sensor in the blood circulation between patient ☺ and pump P, because such pressure sensors serve for the monitoring of the patient and are not suitable for the monitoring of system changes in the tangential flow filter TFF.

In further embodiments, however, on blood side a bubble trap between the pressure sensor and the component can be arranged, and/or on the dialysate side, a filter. The above-described basic principle is not called into question.

The terms "upstream" and "downstream" are to be understood with reference to the flow direction. If a pressure sensor is "upstream", it is located in flow direction before the component, i.e the blood or the dialysate passes at first through the pressure sensor, and then the component. If a pressure sensor is "downstream", then it is located in flow direction after the component, i.e. the blood or the dialysate passes at first through the component and then the pressure sensor. The flow direction can be in the blood circulation and in the dialysis circulation contrary to each other.

The inventive devices for the treatment of blood can comprise further an ultrafiltration pump UFP, a balance chamber system BK or balance chamber BK and/or a unit for the analysis of the measured pressure signals. The ultrafiltration pump is needed for the continuously controlled ultrafiltration and removes from the closed system a precisely set amount of fluid. The same amount that is removed from the dialysate circulation is removed in the tangential flow filter TFF from the blood by means of low pressure. For the balancing of the incoming and outgoing flows the balance chamber BK is responsible, thus it is ensured that no fluid is removed from the patient or supplied to the patient unintentionally. The balance chamber can be divided by a flexible separation wall into two chamber halves, which are filled alternately with the ultrafiltrate which is removed from the dialysate circulation, wherein the content of the respective other chamber half is discarded. Optionally, the inventive device further comprises a drip chamber. The drip chamber will help to prevent the intrusion of air into the downstream tubes, by means of a fluid layer acting as an air lock at the bottom of the drip chamber.

The pressure sensors [PB1], [PB2], [PD1] and [PD2] are characterized advantageously in that they have a sampling rate of at least 20 Hz. A sampling rate of 20 Hz means that a pressure measurement per pressure sensor is performed 20 times per seconds.

The terms "on dialysate side" and "on blood side" describe the two circulations which are passed along to one another in the tangential flow filtration, usually by the countercurrent principle, but if necessary, in parallel to the blood stream together. Into the hollow fibers of the filter membrane blood/plasma are supplied via a first fluid circulation which flows through them lengthwise. By a second fluid circulation, the dialysate is supplied to the outside of the hollow fibers. Both circulations are separated from each other and are only in contact with each other through the filter membrane.

The term "tolerance range" refers to a range around a ideally assumed expected value of a pressure signal at a given pressure measuring point at a given time during the treatment, within which deviations of the expected value can be tolerated. This tolerance range is determined before the beginning of a dialysis session, but can also be determined as brand-specific already by the manufacturer. Here, these may be absolute values, or an absolute or percentage range around an expected value, wherein the expected value is determined during the dialysis session, retrieved from data stored on the central processing unit or input previously. Measured values that fall within such a determined tolerance range, are described as "remained unchanged".

The term "pattern", as used herein, refers to a mathematical, electronic and/or graphical representation form of the trend of several quotients and/or differences and/or absolute values of pressure signals over the time. From this pattern the evaluation "rapidly increasing", "increasing", "remained unchanged", "decreasing" or "rapidly decreasing can directly be derived".

The term "any possible pattern" means that only some of said pattern can occur through disturbances in the operation at a blood treatment unit. Other patterns cannot occur due to logical reasons or would be caused by a failure in the system which is not related with the invention, such as a malfunctioning pressure measuring device. Such constellation should be not covered by the term "any possible pattern" and require in the present invention no particular consideration.

The term "pattern table" refers to a mathematic, electronic and/or graphical register or a corresponding matrix, wherein for every conceivable case combination of the evaluations increasing, remained unchanged or decreasing for the up to four measuring points, an indication about the finding of the disturbance and a proposed measure for its elimination is stored. In preferred embodiments not only a qualitative indication about the possible disturbance is cited in the pattern table, but also a measure or a formula in order to calculate the scope from the measured values of the pressure signals the variable parameters need to be readjusted at the blood treatment unit. In further preferred embodiments, according to a comparison of the pattern determined from the current pressure signals with the pattern table, the recommended qualitative and/or quantitative adjustment is performed automatically. This requires a transmission of the measure of adjustment from the central processing unit to the at least one actuator at the blood treatment unit in order to implement the determined adjustment measure.

The elimination of a disturbance of the flow resistance in transmembrane direction may consist in a regulation of the blood flow, a regulation of the dialysate flow, a coordinated control of blood and dialysate flow, a transmembrane purging process, a purging process on blood side, a change of the treatment time, a regulation of the ultrafiltration rate, a combination of the aforementioned or an exchange of the filter module. The exchange of the filter module can be performed only by interruption or after the end of the dialysis session. All other measures can be induced online during the dialysis session.

The elimination of a disturbance of flow resistance in blood flow direction may consist of a regulation of the blood flow, a regulation of the dialysate flow, a coordinated control of blood and dialysate flow, a blood dilution before the filter (predilution), a purging on blood side, a transmembrane purging, an addition of anticoagulants, a change of the treatment time, a regulation of the ultrafiltration rate, a combination of the aforementioned or an exchange of at least one tube or one tube system.

The exchange of a tube or a tube system can be performed only by interruption or after the end of the dialysis session. Occasionally a disturbance may consist of the bending or collapsing of one or more tubes. These errors can be eliminated usually relatively easy depending on the type of dialysis device. As in the previous case, however, most of the other measures can be induced online during the dialysis session.

A schematic flow system with the following components is shown in FIG. 1. A pump P, preferably a peristaltic pump, generates the expected flow in the extracorporeal circulation. In the blood circulation, as shown in dashed lines, the blood of the patient ☺ at first passes through the pump P, then through the first pressure sensor on blood side [PB1], the tangential flow filter TFF and before it flows back into the patient ☺ through yet another pressure sensor [PB2]. By the countercurrent principle, dialysate is pumped through the filter TFF. In the dialysis circulation, as shown in solid lines, there is the first dialysate pressure sensor [PD1] in flow direction before the filter TFF and the second pressure sensor [PD2] after the filter TFF. For the balancing of incoming and outgoing flows the balance chamber BK is provided, thus it is ensured that no fluid is removed from the patient ☺ or supplied to him unintended. The weight loss prescribed for therapy is produced by the ultrafiltration pump UFP, which bypasses the balance chamber BK.

The pressure progress of pressures PB1, PB2 and PD2 under different treatment conditions can be understood on the basis of FIG. 2. A and B are the pressure curves of a dialyzer with high permeability at UF=0 (A) and UF>0 (B). C and D are the pressure curves of a dialyzer with low permeability at UF=0 (C) and UF>0 (D). The dialyzer geometry (fiber length, fiber internal diameter and number of fibers) remains constant. In A the pressure signal PB1 is shown before the dialyzer. It is in amplitude and absolute value the strongest signal. PB2 and PD2 are in their amplitude and the absolute value below the latter. It is also shown that the signals are shifted in phase against PB1, but have no phase shift among each other.

Comparing the signals from A with those from B, it is shown that the phase has not changed. The situation of pressures PB1 and PB2 is unchanged. The absolute value of PD2 is however lower and the amplitude of PB1 is reduced, which can be explained by the increase of the UF rate. The disturbance impressed by the pressure signal PD2 is generated in this case by the UF pump, a gear pump.

Comparing C and D with one another, it is shown that the increase of the UF rate has the same effects. The high frequency pulses occurring in PD2 specially at UF>0 are in turn caused by the UF pump.

Comparing the different permeabilities at the same UF rates, it is shown that the amplitudes on the blood side (at PB1 and PB2) are larger at lower permeability. The reason is that the lack of transfer to the dialysate side, which is caused by an increased transmembrane flow resistance, must be compensated by an increase in the pulse amplitudes on blood side.

The pressure progress for the pressures PB1, PB2 and PD1 at a blood flow of 100 ml/min is shown in FIG. 3. The pressure curves were in each case compared to a sine function whose minima coincide with the minima of the pressure signal. Thus the periodicity, the basis for calculation of the phase shift as well as the frequency analysis is made clear.

The function with which the sine function was adjusted is:

$$G = A \cdot \sin(2 \cdot \pi \cdot f \cdot t + \phi) + B$$

(A: amplitude in mm Hg, f: frequency in Hz, t: time, φ: initial phase in radian, B: offset)

A frequency analysis is shown exemplary by a pressure signal of PB1 (FIG. 4). The progress of the pressure signal corresponds to that of FIGS. 2 A-D. In the graphic above the time progress over 60 s is shown. In the middle graph a section of the corresponding frequency spectrum is plotted. The graphic below shows the comparison between the amplitudes of the spectra of the pressure signal PBE for different permeabilities. The reduction of the permeability increases the frequency amplitude of the pressure receiver [PB1] on blood side. This is particularly clear for the basic oscillation as well as the first higher orders.

The invention refers also to a device that is capable of carrying out the above-described measuring method and adjustment measures. Such a device is a blood treatment system.

A "blood treatment system", as used herein, comprises a blood treatment unit, whose centerpiece is a tangential flow filter TFF, at least two pressure sensors which are selected from the group consisting of [PB1], [PB2], [PD1] and [PD2], and a central processing unit, wherein the at least two pressure sensors are connected with the central processing unit for the transmission of the measured values and the central processing unit is capable of analyzing and displaying the incoming measured values in such a way that a differentiation of flow resistance changes in transmembrane direction, dialysate flow direction and blood flow direction is possible in the blood treatment system.

Thus, the invention refers also to a device comprising the following:

A blood treatment unit and at least two pressure sensors which are selected from the group consisting of [PB1], [PB2], [PD1] and [PD2], wherein [PB1] represents the pressure sensor in the blood circulation before the blood inlet into the tangential flow filter TFF, [PB2] represents the pressure sensor in the blood circulation after the blood outlet from the tangential flow filter TFF, [PD1] represents the pressure sensor in the dialysate circulation before the dialysate inlet into the tangential flow filter TFF and [PD2] represents the pressure sensor in the dialysate circulation after the dialysate outlet from the tangential flow filter TFF and a central processing unit, wherein the device is suitable to perform a method for the differentiation of disturbances of the flow resistance in a blood treatment unit with a tangential flow filter TFF, which comprises the following steps:

a) measuring at least two pressure signals selected from the group consisting of (PB1, PB2, PD1, PD2), which are measured at least two pressure sensors, which are selected from the group consisting of [PB1], [PB2], [PD1] and [PD2], wherein [PB1] represents the pressure sensor in the blood circulation before the blood inlet into the tangential flow filter TFF and PB1 represents the pressure measured at the pressure sensor [PB1], [PB2] represents the pressure sensor in the blood circulation after the blood outlet from the tangential flow filter TFF and PB2 represents the pressure measured at the pressure sensor [PB2], [PD1] represents the pressure sensor in the dialysate circulation before the dialysate inlet into the tangential flow filter TFF and PD1 represents the pressure measured at the pressure sensor [PD1] and [PD2] represents the pressure sensor in the dialysate circulation after the dialysate outlet from the tangential flow filter TFF and PD2 represents the pressure measured at the pressure sensor [PD2];

b) calculating the quotients and/or the differences from the pressure signals measured according to step a), wherein the quotients and/or the differences are calculated from the pressure signals selected from the group consisting of (PB1, PB2) and/or (PB1, PD1) and/or (PB1, PD2) and/or (PB2, PD1) and/or (PB2, PD2) and/or (PD1, PD2) and/or (PB1, PDM) and/or (PB2, PDM) and/or (PD1, PBM) and/or (PD2, PBM) and/or (PDM, PBM) in a central processing unit, wherein with PBM or PDM the respective average value from (PB1,PB2) or (PD1, PD2) is represented;

c) at least one time-shifted repeating of the steps a) and b), wherein it is measured at the same at least two pressure sensors as in the previous measurement and from the measured pressure signals the same quotients and/or differences are calculated;

d) generating at least one time trend from the measured pressure signals selected from the group consisting of: (PB1, PB2, PD1, PD2) and/or the calculated differences, and/or quotients of the pressure signals (PB1, PB2) and/or (PB1, PD1) and/or (PB1, PD2) and/or (PB2, PD1) and/or (PB2, PD2) and/or (PD1, PD2) and/or (PB1, PDM) and/or (PB2, PDM) and/or (PD1, PBM) and/or (PD2, PBM) and/or (PDM, PBM);

e) evaluating the at least one time trend, whether a change of the at least one time trend has occurred beyond a tolerance range;

f) generating a pattern for the evaluation of the at least one time trend;

g) assigning the pattern to a disturbance condition; and h) displaying the disturbance on a display device of the central processing unit.

Further, the invention refers also to a device which comprises the following: A blood treatment unit and at least three pressure sensors which are selected from the group consisting of [PB1], [PB2], [PD1] and [PD2], wherein [PB1] represents the pressure sensor in the blood circulation before the blood inlet into the tangential flow filter TFF, [PB2] represents the pressure sensor in the blood circulation after the blood outlet from the tangential flow filter TFF, [PD1] represents the pressure sensor in the dialysate circulation before the dialysate inlet into the tangential flow filter TFF and [PD2] represents the pressure sensor in the dialysate circulation after the dialysate outlet from the tangential flow filter TFF and a central processing unit, wherein the device is suitable to perform a method for the differentiation of disturbances of the flow resistance in a blood treatment unit with a tangential flow filter TFF, which comprises the following steps:

a) measuring at least three pressure signals selected from the group consisting of (PB1, PB2, PD1, PD2), which are measured at least three pressure sensors, which are selected from the group consisting of [PB1], [PB2], [PD1] and [PD2], wherein [PB1] represents the pressure sensor in the blood circulation before the blood inlet into the tangential flow filter TFF and PB1 represents the pressure measured at the pressure sensor [PB1], [PB2] represents the pressure sensor in the blood circulation after the blood outlet from the tangential flow filter TFF and PB2 represents the pressure measured at the pressure sensor [PB2], [PD1] represents the pressure sensor in the dialysate circulation before the dialysate inlet into the tangential flow filter TFF and PD1 represents the pressure measured at the pressure sensor [PD1] and [PD2] represents the pressure sensor in the dialysate circulation after the dialysate outlet from the tangential flow filter TFF and PD2 represents the pressure measured at the pressure sensor [PD2];

b) calculating the quotients and/or the differences from the pressure signals measured according to step a), wherein the quotients and/or the differences are calculated from the pressure signals selected from the group consisting of (PB1, PB2) and/or (PB1, PD1) and/or (PB1, PD2) and/or (PB2, PD1) and/or (PB2, PD2) and/or (PD1, PD2) and/or (PB1, PDM) and/or (PB2, PDM) and/or (PD1, PBM) and/or (PD2, PBM) and/or (PDM, PBM) in a central processing unit, wherein with PBM or PDM the respective average value from (PB1,PB2) or (PD1, PD2) is represented;

c) at least one time-shifted repeating of the steps a) and b), wherein it is measured at the same at least three pressure sensors as in the previous measurement and from the measured pressure signals the same quotients and/or differences are calculated;

d) generating at least one time trend from the measured pressure signals selected from the group consisting of: (PB1, PB2, PD1, PD2) and/or the calculated differences, and/or quotients of the pressure signals (PB1, PB2) and/or (PB1, PD1) and/or (PB1, PD2) and/or (PB2, PD1) and/or (PB2, PD2) and/or (PD1, PD2) and/or (PB1, PDM) and/or (PB2, PDM) and/or (PD1, PBM) and/or (PD2, PBM) and/or (PDM, PBM);

e) evaluating the at least one time trend, whether a change of the at least one time trend has occurred beyond a tolerance range;

f) generating a pattern for the evaluation of the at least one time trend;

g) assigning the pattern to a disturbance condition; and h) displaying the disturbance on a display device of the central processing unit.

Further, the invention refers also to a device, which comprises the following:

A blood treatment unit and four pressure sensors [PB1], [PB2], [PD1] and [PD2], wherein [PB1] represents the pressure sensor in the blood circulation before the blood inlet into the tangential flow filter TFF, [PB2] represents the pressure sensor in the blood circulation after the blood outlet from the tangential flow filter TFF, [PD1] represents the pressure sensor in the dialysate circulation before the dialysate inlet into the tangential flow filter TFF and [PD2] represents the pressure sensor in the dialysate circulation after the dialysate outlet from the tangential flow filter TFF and a central processing unit, wherein the device is suitable to perform a method for the differentiation of disturbances of the flow resistance in a blood treatment unit with a tangential flow filter TFF, which comprises the following steps:

a) measuring four pressure signals (PB1, PB2, PD1, PD2), which are measured at four pressure sensors ([PB1], [PB2], [PD1] and [PD2]), wherein [PB1] represents the pressure sensor in the blood circulation before the blood inlet into the tangential flow filter TFF and PB1 represents the pressure measured at the pressure sensor [PB1], [PB2] represents the pressure sensor in the blood circulation after the blood outlet from the tangential flow filter TFF and PB2 represents the pressure measured at the pressure sensor [PB2], [PD1] represents the pressure sensor in the dialysate circulation before the dialysate inlet into the tangential flow filter TFF and PD1 represents the pressure measured at the pressure sensor [PD1] and [PD2] represents the pressure sensor in the dialysate circulation after the dialysate outlet from the tangential flow filter TFF and PD2 represents the pressure measured at the pressure sensor [PD2];

b) calculating the quotients and/or the differences from the pressure signals measured according to step a), wherein the quotients and/or the differences are calculated from the pressure signals selected from the group consisting of (PB1, PB2) and (PB1, PD1) and (PB1, PD2) and (PB2, PD1) and (PB2, PD2) and (PD1, PD2) and (PB1, PDM) and (PB2, PDM) and (PD1, PBM) and (PD2, PBM) and (PDM, PBM) in a central processing unit, wherein with PBM or PDM the respective average value from (PB1,PB2) or (PD1, PD2) is represented;

c) at least one time-shifted repeating of the steps a) and b), wherein it is measured at the same four pressure sensors as in the previous measurement and from the measured pressure signals the same quotients and/or differences are calculated;

d) generating the time trends from the measured pressure signals (PB1, PB2, PD1, PD2) and/or the calculated differences, and/or quotients of the pressure signals (PB1, PB2) and (PB1, PD1) and (PB1, PD2) and (PB2, PD1) and (PB2, PD2) and (PD1, PD2) and (PB1, PDM) and (PB2, PDM) and (PD1, PBM) and (PD2, PBM) and (PDM, PBM);

e) evaluating the time trends, whether a change of the time trends has occurred beyond a tolerance range;

f) generating a pattern for the evaluation of the time trends;

g) assigning the pattern to a disturbance condition; and h) displaying the disturbance on a display device of the central processing unit.

In preferred embodiments, said blood treatment system comprises additionally an ultrafiltration pump and/or a balance chamber system.

According to aspects of the invention, the pressure sensors [PB1], [PB2], [PD1] and [PD2] in this blood treatment system have each a sampling rate of at least 20 Hz.

BRIEF DESCRIPTION OF THE DRAWINGS

FIG. 3: Pressure progress for the pressures PB1, PB2 and PD2 at a blood flow of 100 ml/min. Sine function fitted to it.

FIG. 5: Signal PD2 at high permeabilities (above). Comparison of frequency spectra at a high and a reduced permeability (below).

FIG. 6: Pattern constellations for occurring pressure changes (absolute pressure and quotients)
+ increases
++ increases fast
− decreases
−− decreases fast
0 remains unchanged.

FIG. 7: Pattern constellations for occurring pressure changes (absolute pressures and differences)
+ increases
++ increases fast
− decreases
−− decreases fast
0 remains unchanged.

EXAMPLES

Example 1

Analysis of the Amplitudes of the Pressure Pulses

Figure 1:
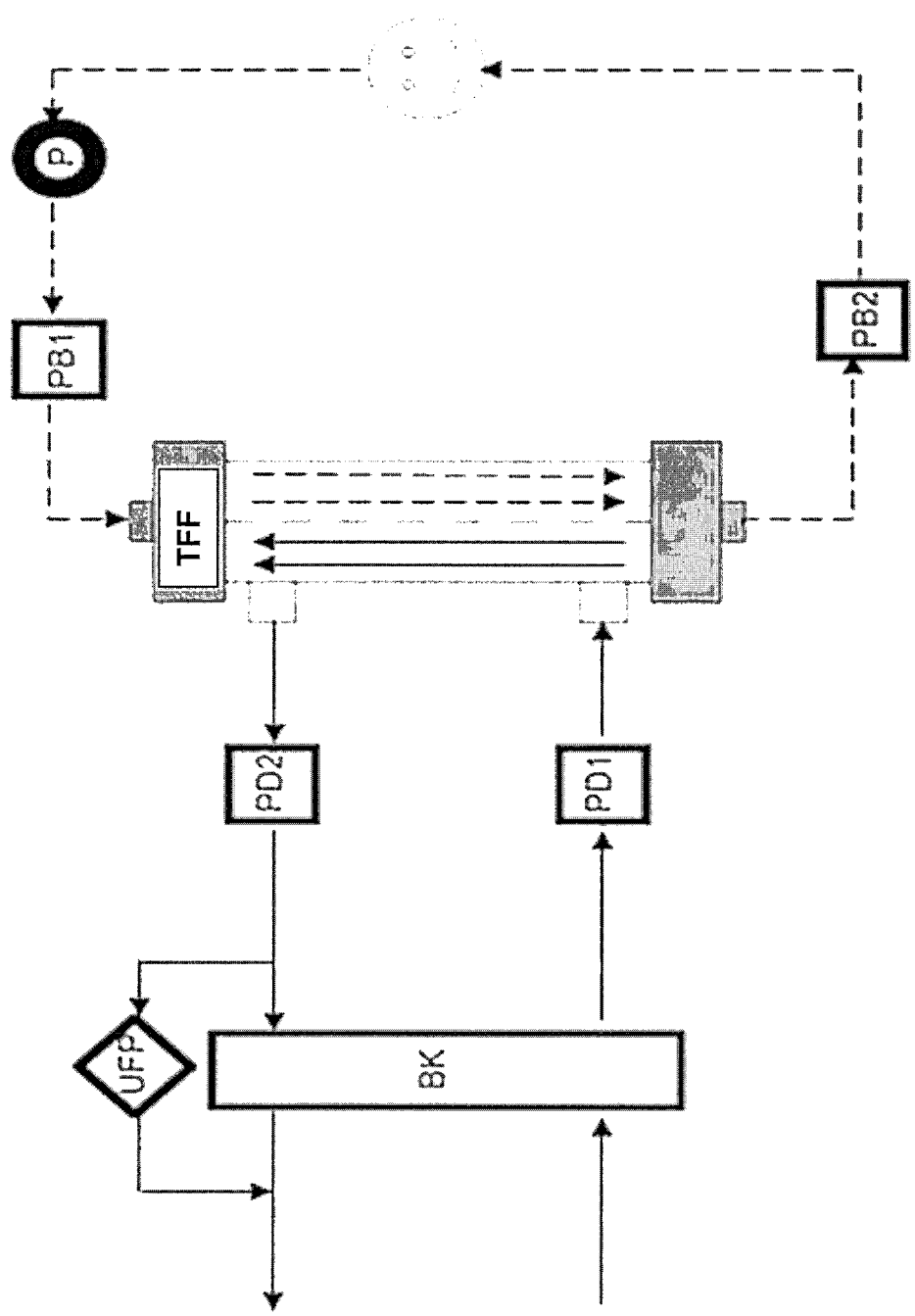
FIG. 1: Scheme for a typical flow system according to aspects of the invention.
Figure 2:
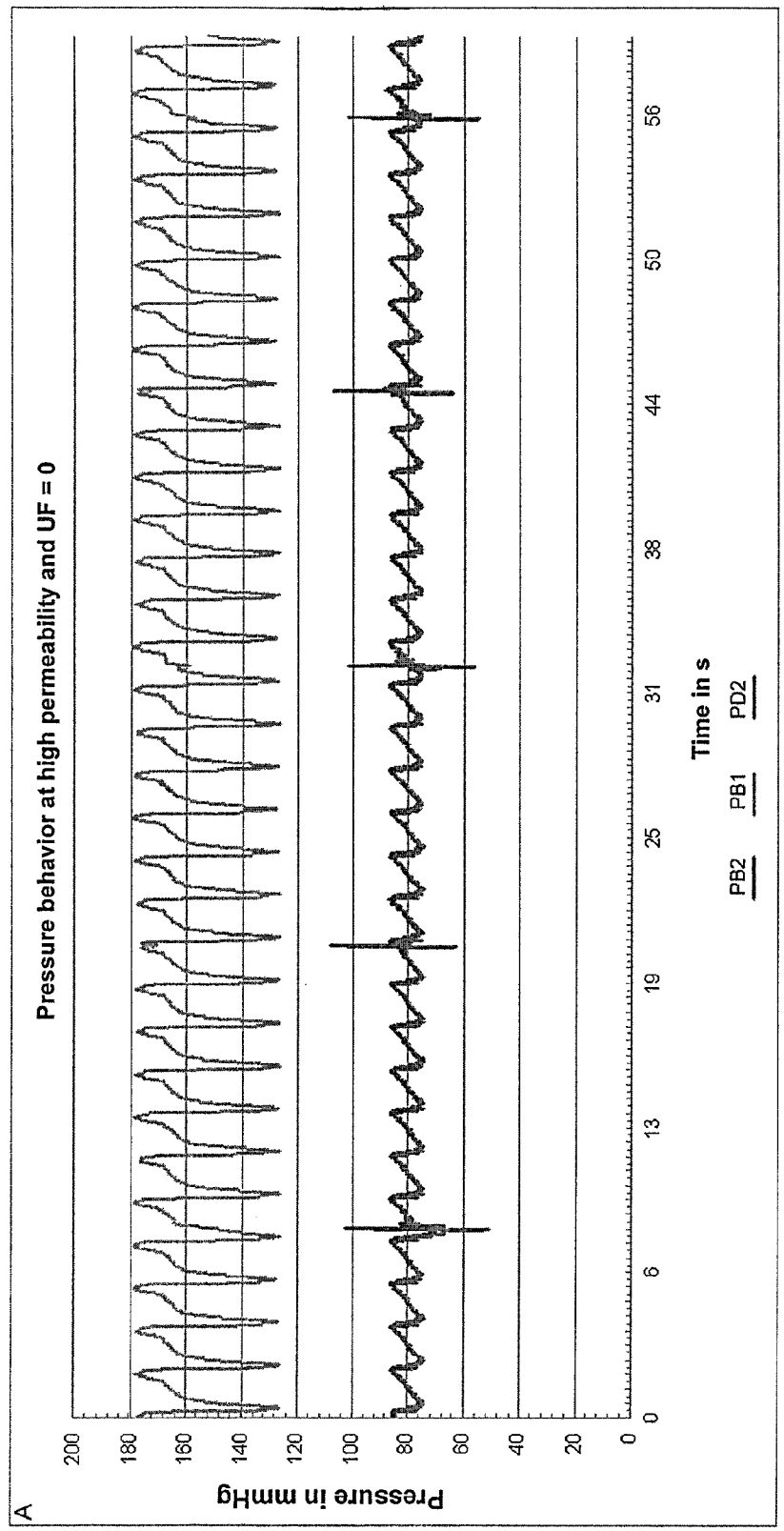
FIGS. 2 A-D: Pressure progress of the pressures PB1, PB2 and PD2 under various treatment conditions
2A: Pressure behavior at high permeability and UF=0
2B: Pressure behavior at high permeability and UF>0
2C: Pressure behavior at low permeability and UF=0
2D: Pressure behavior at low permeability and UF>0.
Figure 2:
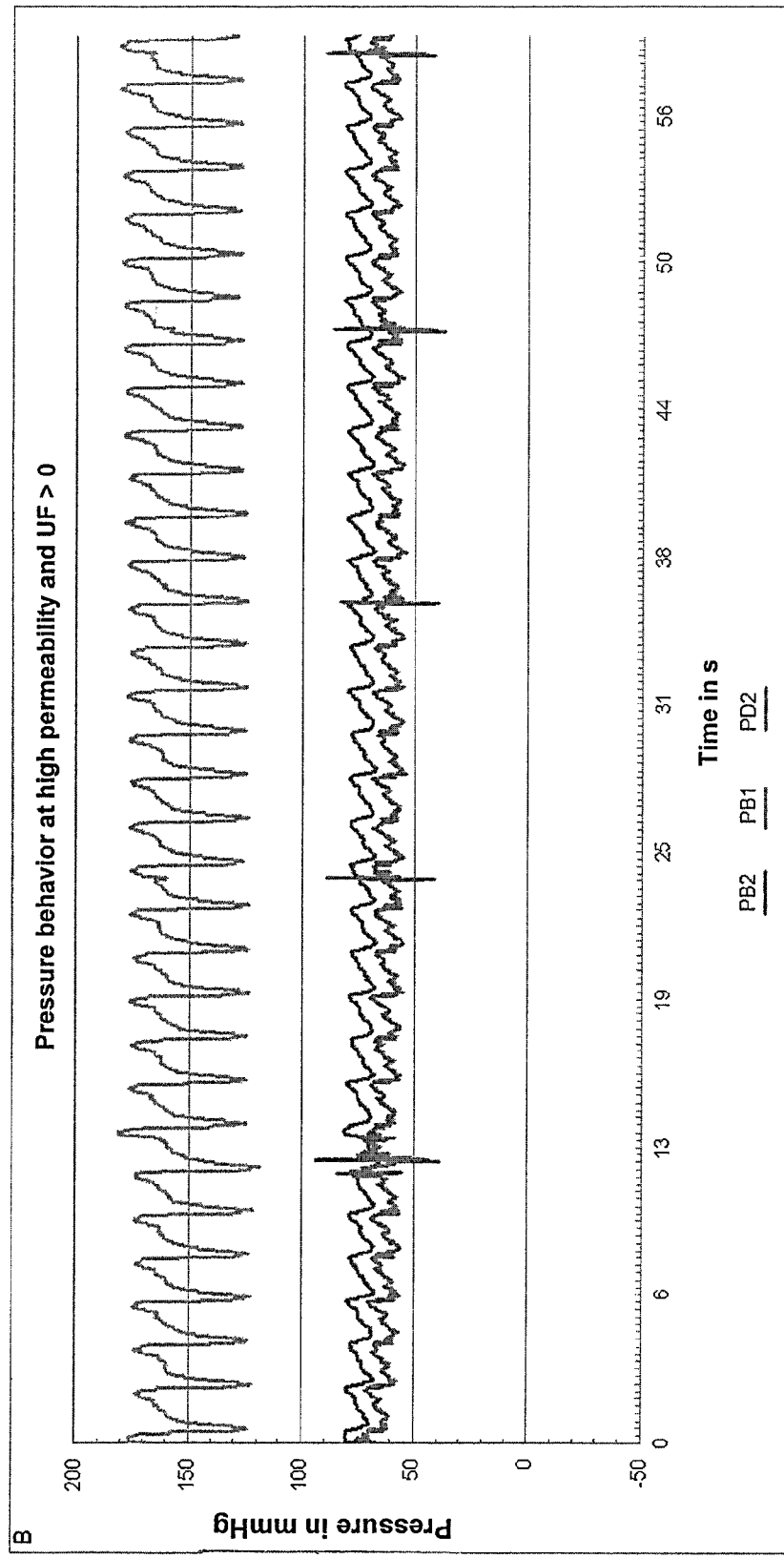
Figure 2:
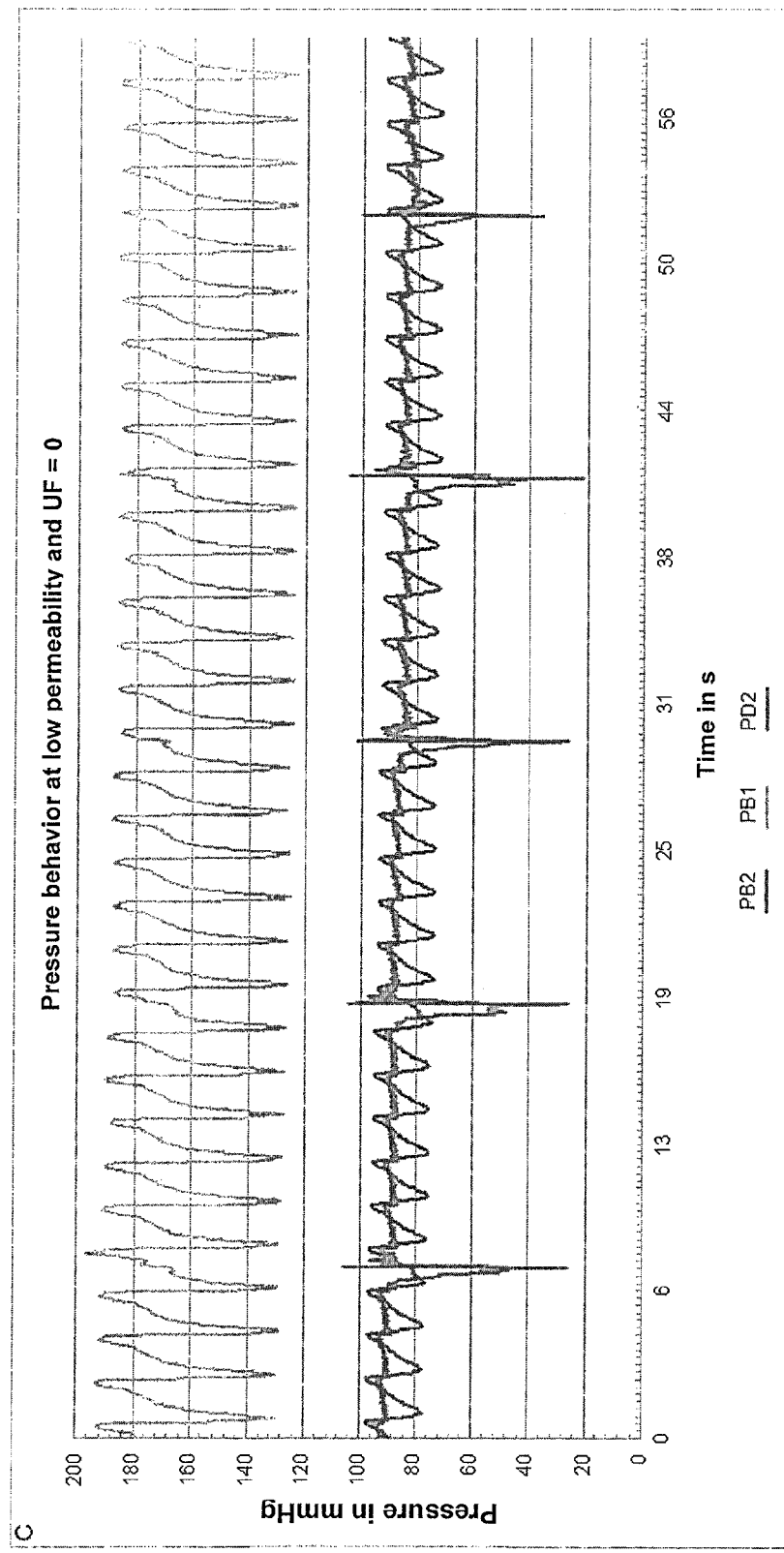

A periodic pressure progress is divided into individual pressure pulses and the amplitude of each pulse is determined from the minimum and maximum value. Therefore the periodic occurring minima of one pressure progress are determined. As a pressure pulse, a section from a minimum to the following minimum is considered. The width of the periodic pressure pulses is determined by the structure of the blood pump and the blood flow (BF). The pulse width is the same for all pressures and ultrafiltration rate (UF rate) at fixed BF, which however grow with increasing BF. For each pulse, the minimum and the maximum pressure are read. The amplitude is given by the difference of these extreme values. The ratios $A_{PD1}/A_{PB1}$ and $A_{PD2}/A_{PB1}$ as well as $A_{PD1}/A_{PB2}$ and $A_{PD2}/A_{PB2}$ show a significant increase with increasing fiber permeability. This is clearly shown in FIG. 2. With increasing BF the pressure pulses increase, but ratios remain substantially constant. An increase of the UF rate has the same effects on the pressure behavior as described above the permeability. In both cases, the transmembrane momentum transfer is improved. A change of the resistance in blood flow direction is reflected as expected in a reduction of the ratio of amplitudes from $A_{PB2}/A_{PB1}$. Since the attenuation in flow direction is increased, $A_{PB2}$ decreases. As expected, the amplitudes on the dialysate side hence increase in the same manner as the mentioned dependent ratios. The same behavior is shown in the reverse direction, when on the dialysate side pulses are generated, for example by a balance system for compensation of the ultrafiltration. Therefore, these can also be used for the characterization of the system, both in transmembrane and in dialysate flow direction.

Example 2

Analysis of the Phase Shift of the Pressure Signals

The pressure progresses can be approximated well in respect to the positions of the minima by a sine function with fixed frequency and phase shift. The frequency is identical for the respective pressures and is determined by the blood flow and the blood pump operating periodically, usually a peristaltic pump. The reciprocal of the frequency corresponds to the time width of an individual pressure pulse. Between the individual pressure progresses there is a phase shift, which is dependent, inter alia, on the permeability. The fill level of the bubble trap and the length of the tube system also have an influence and should therefore be kept constant during the measurements. With decreasing permeability, the phase shift of PB1 to PD1 and PD2 is larger, whereas that of PB1 to PB2 decreases.

During the use of a high-flux dialyzer (dialysis filter) with a hydraulic permeability of 275 ml/(h m² mmHg) both PB2 and PD2 are shifted by 0.53 rad against PB1 (see FIG. 3). If the permeability is changed up to that of a low-flux dialyzer (14 ml/(h m² mmHg)), PB2 is shifted against PB1 by 0.38 rad and PD2 phase shifted by 0.65 rad against PB1. This results from the changed flow resistances in the respective directions.

Example 3

Analysis of the Frequency Spectra of the Pressure Signals

The bases for calculation are the values of the complex amplitudes $|c_n|$ of the individual Fourier terms to the different frequencies according to $$F(t) = \sum_{-\infty}^{\infty} c_n \cdot e^{(i \cdot 2 \cdot \pi \cdot n \cdot f \cdot t)}$$

(i=imaginary unit, n=counting parameters, f=frequency, t=time).

The amplitude values are normalized to the vector length proportional for the record time of the transformed signal in order to produce comparability.

Figure 4:
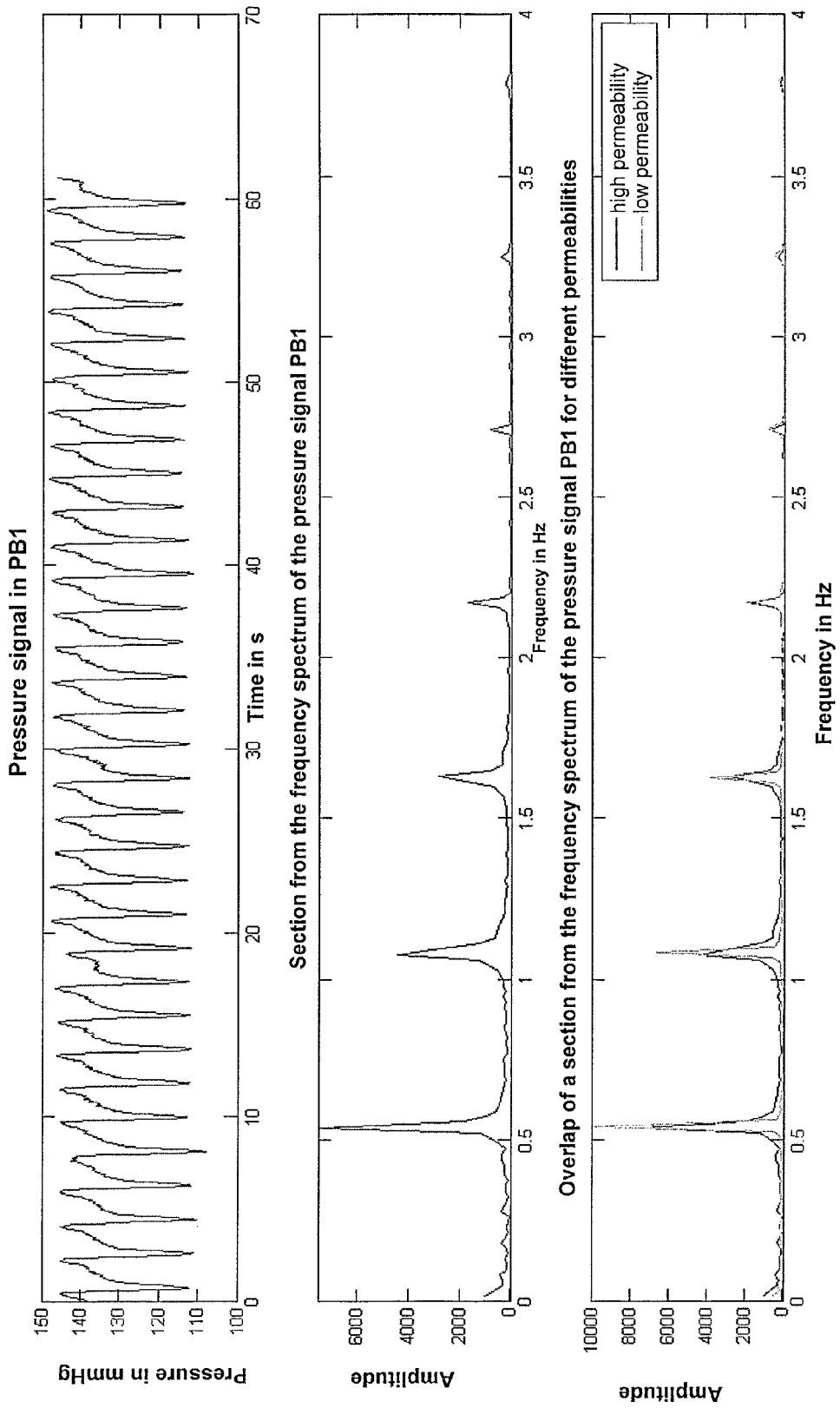
FIG. 4: Frequency analysis of the pressure signal PB1.

The frequency spectra have a regular progress and show amplitude maxima in the basic frequency and integer multiples thereof. The frequencies are dependent on the blood flow. A doubling of the blood flow from 100 ml/min to 200 ml/min leads for example to a doubling of the basic frequency of about 0.27 Hz to 0.54 Hz. The amplitude value $|c_n|$ is greater for the pressures on blood side PB1 and PB2 with decreasing permeability and for the pressures on dialysate side (PD1 and PD2) it occurs inversely In FIG. 4 it is shown how the permeability change as described in Example 2 affects the frequency spectrum of the pressure signal PB1. This is shown in an analogous manner in FIG. 5 for PD2.

Example 4

Detection of a Disturbance in the Form of a Constriction in the Tube System Between [PB1] and the Filter in a Blood Treatment System After the beginning of the treatment with a dialysis device after 5 min preliminary lead time at pressure sensors [PB1], [PB2], [PD1] and [PD2], the following pressure signals PB1=148 mmHg, PB2=61 mmHg, PD1=90 mmHg and PD2=83 mmHg can be measured. The measurement is performed with pressure sensors which have a sample rate of 20 Hz.

After 30 minutes, the pressure signal at the [PB1] suddenly increases within seconds to 207 mmHg, while all other pressure signals remain constant. This is furthermore reflected in an increase in the transmembrane pressure (TMP) from 18 to 48. This could be misinterpreted by the person skilled in the art as significant deterioration of filter permeability, e.g. as formation of a secondary membrane, because he trusts in the TMP.

The consideration of the entity of the measured pressure signals and the quotients and/or the differences of the time trend indicate to the contrary that all pressure sensors show an unchanged trend of the measured pressure signals except for the pressure sensor [PB1], which has a fast increasing trend from 148 mmHg to 207 mmHg. The further calculation of the quotients and of the differences of the measured pressure signals and the generation of the time trends indicate in this case that the time trends of the quotients of the measured pressure signals (PB1, PB2), (PB1, PD1), (PB1, PD2), (PB1, PDM), (PBM, PD1), (PBM, PD2) and (PBM, PDM) increase fast, whereas the time trends of the quotients of the measured pressure signals (PB2, PD1), (PB2, PD2), (PB2, PDM) and (PD1, PD2) have remained unchanged.

From this pattern comprising the trends of the measured pressure signals and the trends of the quotients and/or differences of the measured pressure signals, it is immediately clear that the disturbance of the filter permeability cannot be the cause of the disturbance, but that a constriction in the tube system between [PB1] and the filter must have occurred. A disturbance of the filter permeability can be excluded, because otherwise also the trends of the quotients of the measured pressure signals from (PB2, PD1), (PB2, PD2) and (PB2, PDM) should have been increased, and it would have come additionally to a faster increase of all trends in total. This is however not the case in the present disturbance, whereby a disturbance in the form of a secondary membrane formation can be excluded. Therefore, a misinterpretation of the disturbance is avoided and the disturbance is correctly detected locally and determined qualitatively.

Example 5

Detection of a Disturbance in the Form of a Constriction in the Venous Needle

After the beginning of the treatment with a dialysis device after 5 min preliminary lead time at the pressure sensors [PB1], [PB2], [PD1] and [PD2], the following pressure signals PB1=155 mmHg, PB2=68 mmHg, PD1=88 mmHg and PD2=77 mmHg can be measured. The measurement is performed with pressure sensors which have a sample rate of 20 Hz.

During the treatment the pressure signals on the blood side increase PB1 from 155 mmHg to 178 mmHg and PB2 from 68 mmHg to 91 mmHG. On the dialysate side the pressure signals increase too. PD1 from 88 mmHg to 111 mmHg and PD2 from 77 mmHg to 100 mmHg.

The further calculation of the quotients and the differences of the measured pressure signals and of the generation of the time trends indicates in this case that the time trends of the quotients of all pressure signals have a decreasing trend, whereas the time trends of the differences of all pressure signals have an unchanged remained trend. This disturbance condition corresponds to a constriction in the venous needle and is detected according to aspects of the invention.

At a constriction in the venous needle, the filter properties do not change, but the dialysis device still yet adjusts the pressures on dialysate side by the same value, since the ultrafiltration flow must be kept constant. The TMP remains also constant. Just as all other ratios, which result from the difference calculation, because all values change equally in absolute terms. But since the relative changes for the respective pressure signals are variably big, the quotients increase, which are formed from the pressure signals. This is particularly clearly in consideration of the TMP (PBM–PDM) and the quotients of pressure on blood and dialysate side.

TMP (before)=the difference from PBM–PDM=29 mmHg
TMP (after)=the difference from PBM–PDM=29 mmHg
The quotient from PBM (before)/PDM (before)=1.35
The quotient from PBM (after)/PDM (after)=1.27

By observation of the trends of the quotients and the differences the constriction in the venous needle is recognized so early as a clogging of the return flow of the blood to the patient, whereby an imminent critical situation by an excessively closed return flow can be prevented, which would otherwise have remained unnoticed.

The invention claimed is:

1. Method for the differentiation of disturbances of the flow resistance in a blood treatment system which comprises the following steps:
   a) measuring at least two pressure signals selected from the group consisting of (PB1, PB2, PD1, PD2), which are measured at least two pressure sensors, which are selected from the group consisting of [PB1], [PB2], [PD1] and [PD2], wherein [PB1] represents the pressure sensor in the blood circulation before the blood inlet into the tangential flow filter TFF and PB1 represents the pressure measured at the pressure sensor [PB1], [PB2] represents the pressure sensor in the blood circulation after the blood outlet from the tangential flow filter TFF and PB2 represents the pressure measured at the pressure sensor [PB2], [PD1] represents the pressure sensor in the dialysate circulation before the dialysate inlet into the tangential flow filter TFF and PD1 represents the pressure measured at the pressure sensor [PD1] and [PD2] represents the pressure sensor in the dialysate circulation after the dialysate outlet from the tangential flow filter TFF and PD2 represents the pressure measured at the pressure sensor [PD2];
   b) calculating the quotients and/or the differences from the pressure signals measured according to step a), wherein the quotients and/or the differences are calculated from the pressure signals selected from the group consisting of (PB1, PB2) and/or (PB1, PD1) and/or (PB1, PD2)

and/or (PB2, PD1) and/or (PB2, PD2) and/or (PD1, PD2) and/or (PB1, PDM) and/or (PB2, PDM) and/or (PD1, PBM) and/or (PD2, PBM) and/or (PDM, PBM) in a central processing unit, wherein with PBM or PDM the respective average from (PB1,PB2) or (PD1, PD2) is represented;

c) repeating, at least once, the steps a) and b), wherein at the same at least two pressure sensors as measured in the previous measurement and from the measured pressure signals the same quotients and/or differences are calculated;

d) generating at least one time trend from the measured pressure signals selected from the group consisting of (PB1, PB2, PD1, PD2) and/or the calculated differences, and/or quotients of the pressure signals (PB1, PB2) and/or (PB1, PD1) and/or (PB1, PD2) and/or (PB2, PD1) and/or (PB2, PD2) and/or (PD1, PD2) and/or (PB1, PDM) and/or (PB2, PDM) and/or (PD1, PBM) and/or (PD2, PBM) and/or (PDM, PBM);

e) evaluating the at least one time trend, whether a change of the at least one time trend has occurred over a tolerance range;

f) generating a pattern for the evaluation of the at least one time trend;

g) assigning the pattern to a disturbance condition, such that a location and type of the disturbance condition within the blood treatment system is determined;

h) displaying the disturbance condition on a display device of the central processing unit; and i) automatically eliminating, with the blood treatment system, the disturbance condition to return the flow resistance to within the tolerance range, if the system determines that the disturbance condition is of the type and location that can be automatically eliminated.

2. Method according to claim 1, wherein the at least two pressure signals can be respectively absolute pressures, relative pressures, absolute pressure differences between two pressure measuring points, relative pressure differences between two pressure measuring points, absolute pressure amplitudes, relative pressure amplitudes, differences between the absolute pressure amplitudes at two pressure measuring points, or differences between the relative pressure amplitudes at two pressure measurement points or a combination thereof.

3. Method according to claim 1, wherein the at least two pressure signals are determined respectively from the analysis of the frequency spectrum of the blood flow.

4. Method for the differentiation of disturbances of the flow resistance in a blood treatment system, which comprises the following steps:

a) measuring, at least two different times, each of at least two pressure signals at least two pressure sensors,
   wherein the pressure signals are selected from the group consisting of PB1, PB2, PD1 and PD2, the pressure sensors are selected from the group consisting of [PB1], [PB2], [PD1] and [PD2],
   [PB1] represents the pressure sensor in the blood circulation before the blood inlet into the tangential flow filter TFF and PB1 represents the pressure measured at the pressure sensor [PB1],
   [PB2] represents the pressure sensor in the blood circulation after the blood outlet from the tangential flow filter TFF and PB2 represents the pressure measured at the pressure sensor [PB2],
   [PD1] represents the pressure sensor in the dialysate circulation before the dialysate inlet into the tangential flow filter TFF and PD1 represents the pressure measured at the pressure sensor [PD1], and
   [PD2] represents the pressure sensor in the dialysate circulation after the dialysate outlet from the tangential flow filter TFF and PD2 represents the pressure measured at the pressure sensor [PD2];

b) calculating of at least two quotients and/or differences from the pressure signals measured time offset according to step a) at the same pressure sensor in a central processing unit,
   wherein the quotients calculated in such a manner according to the pressure sensor, at which the measurement has been carried out, are represented as Q[PB1], Q[PB2], Q[PD1] and Q[PD2] and the differences as $\Delta$[PB1], $\Delta$[PB2], $\Delta$[PD1] and $\Delta$[PD2];

c) calculating at least one quotient and/or at least one difference in the central processing unit from the quotients and/or differences calculated according to step b), wherein the quotients and/or the differences are selected from the group consisting of
   (Q[PB1], Q[PB2]) and/or (Q[PB1], Q[PD1]) and/or (Q[PB1], Q[PD2]) and/or (Q[PB2], Q[PD1]) and/or (Q[PB2], Q[PD2]) and/or (Q[PD1], Q[PD2]) and/or ($\Delta$[PB1], $\Delta$[PB2]) and/or ($\Delta$[PB1], $\Delta$[PD1]) and/or ($\Delta$[PB1], $\Delta$[PD2]) and/or ($\Delta$[PB2], $\Delta$[PD1]) and/or ($\Delta$[PB2], $\Delta$[PD2]) and/or ($\Delta$[PD1], $\Delta$[PD2]) and/or (Q[PB1], ($\Delta$[PB1]) and/or (Q[PB1], ($\Delta$[PB2]) and/or (Q[PB1], ($\Delta$[PD1]) and/or (Q[PB1], ($\Delta$[PD2]) and/or (Q[PB2], ($\Delta$[PB1]) and/or (Q[PB2], ($\Delta$[PB2]) and/or (Q[PB2], ($\Delta$[PD1]) and/or (Q[PB2], ($\Delta$[PD2]) and/or (Q[PD1], ($\Delta$[PB1]) and/or (Q[PD1], ($\Delta$[PB2]) and/or (Q[PD1], ($\Delta$[PD1]) and/or (Q[PD1], ($\Delta$[PD2]) and/or (Q[PD2], ($\Delta$[PB1]) and/or (Q[PD2], ($\Delta$[PB2]) and/or (Q[PD2], ($\Delta$[PD1]) and/or (Q[PD2], ($\Delta$[PD2])
   and/or (Q[PB1], Q[PBM]) and/or (Q[PB2], Q[PBM]) and/or (Q[PD1], Q[PBM]) and/or (Q[PD2], Q[PBM]) and/or ($\Delta$[PB1], Q[PBM]) and/or ($\Delta$[PB2], Q[PBM]) and/or ($\Delta$[PD1], Q[PBM]) and/or ($\Delta$[PD2], Q[PBM]) and/or (Q[PB1], Q[PDM]) and/or (Q[PB2], Q[PDM]) and/or (Q[PD1], Q[PDM]) and/or (Q[PD2], Q[PDM]) and/or ($\Delta$[PB1], Q[PDM]) and/or ($\Delta$[PB2], Q[PDM]) and/or ($\Delta$[PD1], Q[PDM]) and/or ($\Delta$[PD2], Q[PDM]) and/or (Q[PB1], $\Delta$[PBM]) and/or (Q[PB2], $\Delta$[PBM]) and/or (Q[PD1], $\Delta$[PBM]) and/or (Q[PD2], $\Delta$[PBM]) and/or ($\Delta$[PB1], $\Delta$[PBM]) and/or ($\Delta$[PB2], $\Delta$[PBM]) and/or ($\Delta$[PD1], $\Delta$[PBM]) and/or ($\Delta$[PD2], $\Delta$[PBM]) and/or (Q[PB1], $\Delta$[PDM]) and/or (Q[PB2], $\Delta$[PDM]) and/or (Q[PD1], $\Delta$[PDM]) and/or (Q[PD2], $\Delta$[PDM]) and/or ($\Delta$[PB1], $\Delta$[PDM]) and/or ($\Delta$[PB2], $\Delta$[PDM]) and/or ($\Delta$[PD1], $\Delta$[PDM]) and/or ($\Delta$[PD2], $\Delta$[PDM]) and/or (Q[PBM], Q[PDM]) and/or (Q[PBM], $\Delta$[PBM]) and/or (Q[PBM], $\Delta$[PDM]) and/or (Q[PDM], $\Delta$[PBM]) and/or (Q[PDM], $\Delta$[PDM]) and/or ($\Delta$[PBM], $\Delta$[PDM]) and
   wherein Q[PBM] represents the average from Q[PB1] and Q[PB2], Q[PDM] represents the average from Q[PD1] and Q[PD2], $\Delta$[PBM] represents the average from $\Delta$[PB1] and $\Delta$[PB2], $\Delta$[PDM] represents the average from $\Delta$[PD1] and $\Delta$[PD2];

d) repeating, at least once, the steps a), b) and c), wherein at the same at least two pressure sensors as measured in the previous measurement and from the measured pressure signals the same quotients and/or differences are calculated;

e) generating at least one time trend from the measured pressure signals selected from the groups listed in c);

f) evaluating the at least one time trends, whether a change of the at least one time trend has occurred over a tolerance range;

g) generating a pattern for the evaluation of the at least one time trend;

h) assigning the pattern to a disturbance condition, such that a location and type of the disturbance condition within the blood treatment system;

i) displaying the disturbance condition on a display device of the central processing unit; and j) automatically eliminating, with the blood treatment system, the disturbance condition to return the flow resistance to within the tolerance range, if the system determines that the disturbance condition is of the type and location that can be automatically eliminated.

5. Method according to claim 4, wherein the at least one pressure signal can be respectively an absolute pressure, a relative pressure, an absolute pressure difference between two pressure measuring points, a relative pressure difference between two pressure measuring points, an absolute pressure amplitude, a relative pressure amplitude, a difference between the absolute pressure amplitudes at two pressure measuring points, or a difference between the relative pressure amplitudes at two pressure measurement points or a combination thereof.

6. Method according to claim 5, wherein the at least one pressure signal is determined from the analysis of the frequency spectrum of the blood flow.

7. A blood treatment system which comprises a blood treatment unit and at least two pressure sensors which are selected from the group consisting of [PB1], [PB2], [PD1] and [PD2], wherein [PB1] represents the pressure sensor in the blood circulation before the blood inlet into the tangential flow filter TFF, [PB2] represents the pressure sensor in the blood circulation after the blood outlet from the tangential flow filter TFF, [PD1] represents the pressure sensor in the dialysate circulation before the dialysate inlet into the tangential flow filter TFF, and [PD2] represents the pressure sensor in the dialysate circulation after the dialysate outlet from the tangential flow filter TFF and a central processing unit, wherein the at least two pressure sensors are connected with the central processing unit for the transmission of the measured values and the central processing unit is able to analyze and display the incoming measured values such that a differentiation of flow resistance changes in transmembrane direction and blood flow direction in the blood treatment unit occurs according to the method of claim 1.

8. The blood treatment system according to claim 7, which comprises additionally an ultrafiltration pump and a balance chamber system.

9. The blood treatment system according to claim 7, in which the pressure sensors [PB1], [PB2], [PD1] and [PD2] have respectively a sampling rate of at least 20 Hz.

10. The blood treatment system according to claim 8, in which the pressure sensors [PB1], [PB2], [PD1] and [PD2] have respectively a sampling rate of at least 20 Hz.

11. A blood treatment system according to claim 7, wherein the at least two pressure signals can be respectively absolute pressures, relative pressures, absolute pressure differences between two pressure measuring points, relative pressure differences between two pressure measuring points, absolute pressure amplitudes, relative pressure amplitudes, differences between the absolute pressure amplitudes at two pressure measuring points, or differences between the relative pressure amplitudes at two pressure measurement points or a combination thereof.

12. A blood treatment system according to claim 7, wherein the at least two pressure signals are determined respectively from the analysis of the frequency spectrum of the blood flow.

13. A blood treatment system which comprises a blood treatment unit and at least two pressure sensors which are selected from the group consisting of [PB1], [PB2], [PD1] and [PD2], wherein [PB1] represents the pressure sensor in the blood circulation before the blood inlet into the tangential flow filter TFF, [PB2] represents the pressure sensor in the blood circulation after the blood outlet from the tangential flow filter TFF, [PD1] represents the pressure sensor in the dialysate circulation before the dialysate inlet into the tangential flow filter TFF, and [PD2] represents the pressure sensor in the dialysate circulation after the dialysate outlet from the tangential flow filter TFF and a central processing unit, wherein the at least two pressure sensors are connected with the central processing unit for the transmission of the measured values and the central processing unit is able to analyze and display the incoming measured values such that a differentiation of flow resistance changes in transmembrane direction and blood flow direction in the blood treatment unit occurs according to the method of claim 4.

14. The blood treatment system according to claim 13, which comprises additionally an ultrafiltration pump and a balance chamber system.

15. The blood treatment system according to claim 13, in which the pressure sensors [PB1], [PB2], [PD1] and [PD2] have respectively a sampling rate of at least 20 Hz.

16. The blood treatment system according to claim 14, in which the pressure sensors [PB1], [PB2], [PD1] and [PD2] have respectively a sampling rate of at least 20 Hz.

17. A blood treatment system according to claim 13, wherein the at least one pressure signal can be respectively an absolute pressure, a relative pressure, an absolute pressure difference between two pressure measuring points, a relative pressure difference between two pressure measuring points, an absolute pressure amplitude, a relative pressure amplitude, a difference between the absolute pressure amplitudes at two pressure measuring points, or a difference between the relative pressure amplitudes at two pressure measurement points or a combination thereof.

18. A blood treatment system according to claim 13, wherein the at least one pressure signal is determined from the analysis of the frequency spectrum of the blood flow.

* * * * *